(12) United States Patent
Williams et al.

(10) Patent No.: US 10,758,399 B2
(45) Date of Patent: *Sep. 1, 2020

(54) DEVICE, SYSTEM, KIT OR METHOD FOR COLLECTING EFFLUENT FROM AN INDIVIDUAL

(71) Applicant: Bracco Diagnostics Inc., Monroe Township, NJ (US)

(72) Inventors: Robert C. Williams, Fort Salonga, NY (US); Harry Bratton, Queens, NY (US); David J. Vining, Baltimore, MD (US)

(73) Assignee: BRACCO DIAGNOSTICS INC., Princeton, NJ (US)

( * ) Notice: Subject to any disclaimer, the term of this patent is extended or adjusted under 35 U.S.C. 154(b) by 814 days.

This patent is subject to a terminal disclaimer.

(21) Appl. No.: 14/273,066

(22) Filed: May 8, 2014

(65) Prior Publication Data

US 2014/0296806 A1    Oct. 2, 2014

Related U.S. Application Data

(60) Division of application No. 13/267,434, filed on Oct. 6, 2011, now Pat. No. 8,771,245, which is a division (Continued)

(51) Int. Cl.
*A61F 5/451* (2006.01)
*A61M 1/00* (2006.01)
*A61M 13/00* (2006.01)

(52) U.S. Cl.
CPC ............ *A61F 5/451* (2013.01); *A61M 1/008* (2013.01); *A61M 1/0023* (2013.01);

(Continued)

(58) Field of Classification Search
CPC ..... A61F 5/451; A61M 13/00; A61M 13/003; A61M 13/006; A61M 3/02; A61M 3/0204;

(Continued)

(56) References Cited

U.S. PATENT DOCUMENTS 2,539,189 A    1/1951    Garrett
3,177,871 A    4/1965    Meyers (Continued)

FOREIGN PATENT DOCUMENTS

CN    10 1312763 A    11/2008
CN    10 1370420 A    2/2009

(Continued)

OTHER PUBLICATIONS

Office Action for U.S. Appl. No. 13/402,455 dated Jan. 25, 2015.

(Continued)

*Primary Examiner* — Adam Marcetich
(74) *Attorney, Agent, or Firm* — Alston & Bird LLP

(57) ABSTRACT

The present invention relates to a device, method, system and kit for receiving effluent from an individual. In an alternative embodiment, the present invention is directed to a device, method, system and kit for collecting effluent from an individual during a medical or diagnostic procedure including but not limited to, imaging or viewing one or more sections of an individual's gastrointestinal tract. In another alternative embodiment, the effluent is collected in a hollow area in order to prevent the effluent form contaminating a component, device or apparatus used in connection with the medical or diagnostic procedure.

20 Claims, 17 Drawing Sheets

Related U.S. Application Data of application No. 12/029,159, filed on Feb. 11, 2008, now Pat. No. 8,057,448, which is a continuation of application No. 10/497,625, filed as application No. PCT/US02/37384 on Nov. 21, 2002, now Pat. No. 7,361,170.

(60) Provisional application No. 60/332,072, filed on Nov. 21, 2001.

(52) U.S. Cl.
CPC ........ *A61M 1/0052* (2014.02); *A61M 13/003* (2013.01); *A61M 1/0084* (2013.01); *A61M 2209/084* (2013.01); *A61M 2210/1067* (2013.01)

(58) Field of Classification Search
CPC .............. A61M 3/0208; A61M 3/0212; A61M 3/0216; A61M 3/022; A61M 3/0279; A61M 3/0283; A61M 3/0287; A61M 3/0291; A61M 3/0295
See application file for complete search history.

(56) References Cited

U.S. PATENT DOCUMENTS

| | | | |
|---|---|---|---|
| 3,374,762 | A | 3/1968 | Baldwin |
| 3,674,010 | A | 7/1972 | Falenks |
| 3,858,572 | A | 1/1975 | Binard et al. |
| 3,867,941 | A | 2/1975 | Lindemann |
| 3,870,072 | A | 3/1975 | Lindemann |
| 3,885,567 | A * | 5/1975 | Ross .................. A61M 1/0062 604/120 |
| 3,940,237 | A | 2/1976 | Gonzalez et al. |
| 3,943,938 | A | 3/1976 | Wexler et al. |
| 3,982,533 | A | 9/1976 | Wiest |
| 3,982,538 | A * | 9/1976 | Sharpe ................ A61M 1/0049 604/320 |
| 3,982,540 | A * | 9/1976 | Ross .................. A61M 1/0058 604/540 |
| 4,013,076 | A | 3/1977 | Puderbaugh et al. |
| 4,019,515 | A | 4/1977 | Kornblum et al. |
| 4,030,500 | A | 6/1977 | Ronnquist |
| 4,048,992 | A | 9/1977 | Lindemann et al. |
| 4,052,986 | A | 10/1977 | Scaife |
| 4,090,502 | A | 5/1978 | Tajika |
| 4,117,847 | A | 10/1978 | Clayton |
| 4,182,332 | A | 1/1980 | Delaney |
| 4,207,887 | A | 6/1980 | Hiltebrandt et al. |
| 4,260,496 | A | 4/1981 | Beer |
| 4,276,874 | A | 7/1981 | Wolvek et al. |
| 4,391,280 | A | 7/1983 | Miller |
| 4,419,099 | A | 12/1983 | Miller |
| 4,429,693 | A | 2/1984 | Blake et al. |
| 4,448,207 | A | 5/1984 | Parrish |
| 4,459,139 | A * | 7/1984 | vonReis ................ A61M 5/385 210/416.1 |
| 4,464,169 | A | 8/1984 | Semm |
| 4,504,270 | A | 3/1985 | Miller |
| 4,554,078 | A | 11/1985 | Huggins et al. |
| 4,637,814 | A * | 1/1987 | Leiboff ............... A61M 1/0084 604/27 |
| 4,664,114 | A | 5/1987 | Ghodsian |
| 4,676,744 | A | 6/1987 | Wray et al. |
| 4,676,774 | A | 6/1987 | Semm et al. |
| 4,682,979 | A | 7/1987 | Girouard |
| 4,687,002 | A | 8/1987 | Lahr |
| 4,734,109 | A | 3/1988 | Cox |
| 4,758,221 | A | 7/1988 | Jureidini |
| 4,795,429 | A | 1/1989 | Feldstein |
| 4,813,935 | A * | 3/1989 | Haber .................. A61M 25/04 604/103 |
| 4,865,018 | A | 9/1989 | Kanno et al. |
| 4,874,362 | A | 10/1989 | Wiest et al. |
| 4,875,899 | A | 10/1989 | Holtermann |
| 4,883,462 | A | 11/1989 | Williamson et al. |
| 4,902,484 | A | 2/1990 | Martin et al. |
| 4,917,692 | A | 4/1990 | Steer et al. |
| 4,930,997 | A | 6/1990 | Bennett |
| 4,946,720 | A | 8/1990 | Oishi et al. |
| 4,957,486 | A | 9/1990 | Davis |
| 4,963,134 | A * | 10/1990 | Backscheider ..... A61M 1/0023 55/467 |
| 4,971,034 | A | 11/1990 | Doi et al. |
| 4,973,311 | A * | 11/1990 | Iwakoshi ............... A61B 1/015 600/156 |
| 5,006,109 | A | 4/1991 | Douglas et al. |
| 5,019,059 | A | 5/1991 | Goldberg et al. |
| 5,029,580 | A | 7/1991 | Radford et al. |
| 5,061,239 | A | 10/1991 | Shiels |
| 5,084,060 | A | 1/1992 | Freund et al. |
| 5,098,375 | A | 3/1992 | Baier |
| 5,102,416 | A | 4/1992 | Rock |
| 5,131,906 | A | 7/1992 | Chen |
| 5,160,325 | A | 11/1992 | Nichols et al. |
| 5,176,629 | A | 1/1993 | Kullas et al. |
| 5,176,630 | A | 1/1993 | Shilling et al. |
| 5,178,606 | A | 1/1993 | Ognier et al. |
| 5,184,074 | A | 2/1993 | Arakawa et al. |
| 5,196,244 | A | 3/1993 | Beck |
| 5,292,304 | A | 3/1994 | Mantell et al. |
| 5,312,343 | A | 5/1994 | Krog et al. |
| 5,322,070 | A | 6/1994 | Goodman et al. |
| 5,328,458 | A | 7/1994 | Sekino et al. |
| 5,330,486 | A | 7/1994 | Wilk |
| 5,360,396 | A | 11/1994 | Chan |
| 5,364,363 | A | 11/1994 | Pearson et al. |
| 5,365,928 | A | 11/1994 | Rhinehart et al. |
| 5,382,229 | A | 1/1995 | Grabenkort et al. |
| 5,383,456 | A | 1/1995 | Arnold et al. |
| 5,405,319 | A | 4/1995 | Abell et al. |
| 5,411,474 | A | 5/1995 | Ott et al. |
| 5,423,741 | A | 6/1995 | Frank |
| 5,433,216 | A * | 7/1995 | Sugrue ............... A61B 5/14539 600/591 |
| 5,439,441 | A | 8/1995 | Grimsley et al. |
| 5,458,586 | A * | 10/1995 | Adiletta ............. A61M 1/0049 604/326 |
| 5,487,376 | A | 1/1996 | Yabe et al. |
| 5,549,546 | A | 8/1996 | Schneider et al. |
| 5,569,216 | A | 10/1996 | Kim |
| 5,676,155 | A | 10/1997 | Novak et al. |
| 5,678,568 | A | 10/1997 | Uchikubo et al. |
| 5,688,256 | A | 11/1997 | Surratt et al. |
| 5,720,717 | A | 2/1998 | D'Andrea |
| 5,779,662 | A | 7/1998 | Berman |
| 5,788,688 | A | 8/1998 | Bauer et al. |
| 5,800,381 | A | 9/1998 | Ognier |
| 5,800,493 | A | 9/1998 | Stevens et al. |
| 5,817,124 | A | 10/1998 | Karell |
| 5,897,525 | A | 4/1999 | Dey et al. |
| 5,978,697 | A | 11/1999 | Maytal et al. |
| 5,992,419 | A | 11/1999 | Sterzer et al. |
| 6,004,509 | A | 12/1999 | Dey et al. |
| 6,026,684 | A | 2/2000 | Calder |
| 6,059,717 | A | 5/2000 | Dabney |
| 6,066,139 | A | 5/2000 | Ryan et al. |
| 6,068,609 | A | 5/2000 | Ott et al. |
| 6,083,162 | A * | 7/2000 | Vining .................. G06T 7/0012 128/920 |
| 6,136,292 | A | 10/2000 | Pettersson et al. |
| RE36,994 | E | 12/2000 | Anderberg |
| 6,193,649 | B1 | 2/2001 | Takami et al. |
| 6,228,048 | B1 | 5/2001 | Robbins |
| 6,261,227 | B1 | 7/2001 | Takahashi et al. |
| 6,272,366 | B1 | 8/2001 | Vining |
| 6,299,592 | B1 | 10/2001 | Zander |
| 6,315,716 | B1 | 11/2001 | Takami |
| 6,328,690 | B1 | 12/2001 | Takami et al. |
| 6,400,157 | B1 | 6/2002 | Bonanni et al. |
| 6,402,688 | B1 | 6/2002 | Takami et al. |
| 6,402,714 | B1 | 6/2002 | Kraft-Kivikoski |
| 6,407,308 | B1 | 6/2002 | Roe et al. |

(56) References Cited

U.S. PATENT DOCUMENTS

| | | |
|---|---|---|
| 6,433,939 B2 | 8/2002 | Enomoto |
| 6,458,093 B1 | 10/2002 | Gord et al. |
| 6,467,775 B1 | 10/2002 | Denzinger |
| 6,471,638 B1 | 10/2002 | Chang et al. |
| 6,473,943 B1 | 11/2002 | Thacker |
| 6,478,782 B1 | 11/2002 | Wada |
| 6,485,412 B1 | 11/2002 | Byrne |
| 6,554,780 B1 | 4/2003 | Sampson et al. |
| 6,563,633 B2 | 5/2003 | Nakamura et al. |
| 6,632,194 B1 | 10/2003 | Mehner et al. |
| 6,682,479 B1 | 1/2004 | Takahashi et al. |
| 6,824,539 B2 | 11/2004 | Novak |
| 6,866,654 B2 | 3/2005 | Callan et al. |
| 6,950,691 B2 | 9/2005 | Uchikubo |
| 6,975,968 B2 | 12/2005 | Nakamitsu et al. |
| 7,035,681 B2 | 4/2006 | Johnson et al. |
| 7,063,670 B2 | 6/2006 | Sampson et al. |
| 7,066,173 B2 | 6/2006 | Banner et al. |
| 7,147,627 B2 | 12/2006 | Kim et al. |
| 7,148,887 B2 | 12/2006 | Kaufman et al. |
| 7,149,564 B2 | 12/2006 | Vining et al. |
| 7,250,035 B1 | 7/2007 | Ott et al. |
| 7,272,430 B2 | 9/2007 | Uchikubo |
| 7,320,599 B2 | 1/2008 | Morris |
| 7,361,170 B2 | 4/2008 | Williams et al. |
| 7,476,213 B2 | 1/2009 | Uesugi et al. |
| 7,485,114 B2 | 2/2009 | Stiller et al. |
| 7,485,115 B2 | 2/2009 | Nakamura |
| 7,549,421 B2 | 6/2009 | Levi et al. |
| 7,569,027 B2 | 8/2009 | Uesugi et al. |
| 7,654,975 B2 | 2/2010 | Mantell |
| 7,704,223 B2 | 4/2010 | Mantell |
| 7,722,559 B2 | 5/2010 | Uesugi et al. |
| 7,806,850 B2 | 10/2010 | Williams, Jr. et al. |
| 7,918,816 B2 | 4/2011 | Ott et al. |
| 7,931,588 B2 | 4/2011 | Sarvazyan et al. |
| 7,938,793 B2 | 5/2011 | Mantell |
| 7,981,072 B2 | 7/2011 | Uesugi et al. |
| 8,057,448 B2 | 11/2011 | Williams et al. |
| 8,157,763 B2 | 4/2012 | Williams, Jr. et al. |
| 8,414,550 B2 | 4/2013 | Roberts et al. |
| 2001/0037063 A1 | 11/2001 | Albert et al. |
| 2001/0044576 A1 | 11/2001 | Vining |
| 2002/0045153 A1 | 4/2002 | Kaufman et al. |
| 2002/0161304 A1 | 10/2002 | Eide |
| 2002/0169415 A1 | 11/2002 | Staats et al. |
| 2002/0193687 A1 | 12/2002 | Vining et al. |
| 2003/0093503 A1 | 5/2003 | Yamaki et al. |
| 2003/0145849 A1 | 8/2003 | Drinan et al. |
| 2003/0158499 A1 | 8/2003 | Smith et al. |
| 2004/0030367 A1 | 2/2004 | Yamaki et al. |
| 2004/0059393 A1 | 3/2004 | Policker et al. |
| 2004/0102731 A1 | 5/2004 | Blackhurst et al. |
| 2004/0138586 A1 | 7/2004 | Ganz et al. |
| 2004/0193045 A1 | 9/2004 | Scarborough et al. |
| 2004/0230157 A1 | 11/2004 | Perry et al. |
| 2005/0038374 A1 | 2/2005 | Williams, Jr. et al. |
| 2005/0097191 A1 | 5/2005 | Yamaki et al. |
| 2005/0107766 A1 | 5/2005 | Ott et al. |
| 2005/0137529 A1 | 6/2005 | Mantell |
| 2005/0222491 A1 | 10/2005 | Noda et al. |
| 2005/0222534 A1 | 10/2005 | Uesugi et al. |
| 2005/0222535 A1 | 10/2005 | Uesugi et al. |
| 2005/0245803 A1 | 11/2005 | Glenn, Jr. et al. |
| 2006/0004322 A1 | 1/2006 | Uesugi et al. |
| 2006/0030751 A1 | 2/2006 | Uesugi et al. |
| 2006/0047184 A1 | 3/2006 | Banik et al. |
| 2006/0052661 A1 | 3/2006 | Gannot et al. |
| 2006/0055544 A1 | 3/2006 | Morguelan |
| 2006/0058617 A1 | 3/2006 | Sano et al. |
| 2006/0079758 A1 | 4/2006 | Susi |
| 2006/0089571 A1 | 4/2006 | Gertner |
| 2006/0100500 A1 | 5/2006 | Williams |
| 2006/0129087 A1 | 6/2006 | Uesugi et al. |
| 2006/0253098 A1 | 11/2006 | Garabet |
| 2006/0257008 A1 | 11/2006 | Nolle et al. |
| 2007/0106209 A1 | 5/2007 | Williams, Jr. et al. |
| 2007/0112299 A1 | 5/2007 | Smit et al. |
| 2007/0163585 A1 | 7/2007 | Uesugi et al. |
| 2007/0179432 A1 | 8/2007 | Bar Or et al. |
| 2007/0244363 A1 | 10/2007 | Sano et al. |
| 2007/0244424 A1 | 10/2007 | Hameed et al. |
| 2007/0255165 A1 | 11/2007 | Uesugi et al. |
| 2007/0265492 A1 | 11/2007 | Sonnenschein et al. |
| 2007/0282219 A1 | 12/2007 | Holte |
| 2007/0293734 A1 | 12/2007 | Coste-Maniere et al. |
| 2008/0133602 A1 | 6/2008 | Tashiro et al. |
| 2009/0036749 A1 | 2/2009 | Freiburger et al. |
| 2009/0048506 A1 | 2/2009 | Fong-Ichimura et al. |
| 2009/0143644 A1 | 6/2009 | Stiller et al. |
| 2009/0203995 A1 | 8/2009 | Matonick |
| 2010/0022834 A1 | 1/2010 | Noda et al. |
| 2010/0106080 A1 | 4/2010 | Uesugi et al. |
| 2010/0114011 A1 | 5/2010 | Herrmann |
| 2010/0130917 A1 | 5/2010 | Sezeur et al. |
| 2010/0185139 A1 | 7/2010 | Stearns et al. |
| 2010/0228100 A1 | 10/2010 | Vining |
| 2010/0268153 A1 | 10/2010 | Mantell |
| 2010/0268154 A1 | 10/2010 | Vining |
| 2011/0030678 A1 | 2/2011 | Power et al. |
| 2011/0034862 A1 | 2/2011 | Williams, Jr. et al. |
| 2011/0060272 A1 | 3/2011 | Iranitalab |
| 2011/0066078 A1 | 3/2011 | Sarvazyan et al. |
| 2011/0263939 A1 | 10/2011 | Kaye et al. |
| 2012/0016293 A1 | 1/2012 | Hayashi |
| 2012/0130304 A1 | 5/2012 | Barish et al. |
| 2012/0157770 A1 | 6/2012 | Williams et al. |
| 2013/0102882 A1 | 4/2013 | Williams |

FOREIGN PATENT DOCUMENTS

| | | |
|---|---|---|
| CN | 102334973 A | 2/2012 |
| DE | 42 19 859 A1 | 12/1993 |
| DE | 92 18 373 U1 | 1/1994 |
| EP | 0 569 241 A2 | 11/1993 |
| EP | 1101 506 A | 5/2001 |
| FR | 2 673 524 A1 | 9/1992 |
| JP | 48-43279 | 12/1973 |
| JP | 2-17141 | 2/1990 |
| JP | 4-27943 | 3/1992 |
| JP | 4-92249 | 8/1992 |
| JP | 4-297219 | 10/1992 |
| JP | 4-133845 | 12/1992 |
| JP | H05154094 A | 6/1993 |
| JP | H05226193 | 9/1993 |
| JP | 5-344950 A | 12/1993 |
| JP | 07-265261 A | 10/1995 |
| JP | 9-038092 A | 2/1997 |
| JP | 2006-014961 A | 1/2006 |
| JP | 2007-075396 A | 3/2007 |
| JP | 2008-093489 A | 4/2008 |
| JP | 2009-512535 A | 3/2009 |
| JP | 2010-227484 A | 10/2010 |
| WO | WO 00/69511 A | 11/2000 |
| WO | WO 2005/120329 A1 | 12/2005 |
| WO | WO 2006/002635 A1 | 1/2006 |
| WO | WO 2007/050516 A2 | 5/2007 |
| WO | WO 2008/053485 A1 | 5/2008 |
| WO | WO 2009/052100 A2 | 4/2009 |
| WO | WO 2012/071399 A1 | 5/2012 |

OTHER PUBLICATIONS

Office Action for U.S. Appl. No. 13/711,802 dated Jan. 20, 2015.
Office Action for U.S. Appl. No. 14/459,365 dated Feb. 18, 2015.
Notice of Acceptance for Australian Application No. 2011331936 dated Feb. 10, 2015.
Office Action for Chinese Application No. 201180056406.6 dated Jan. 23, 2015.
Search Report for European Application No. EP 14 18 8116 dated Feb. 17, 2015.
Office Action for Japanese Application No. 2013-541016 dated Feb. 10, 2015.

(56) References Cited

OTHER PUBLICATIONS

Office Action for Korean Application No. 10-2013-7016190 dated Dec. 29, 2014.
Office Action for U.S. Appl. No. 11/315,049 dated Mar. 21, 2012.
Canadian Office Action for Application No. 2,642,135; dated Oct. 4, 2011.
Extended European Search Report for European Patent Application No. 05855170.6, dated Jun. 4, 2010.
Third Party Oberservation for Application No. EP 02 789 809.7 dated Oct. 15, 2010.
Intention to Grant for Application No. EP 02 789 809.7 dated Apr. 27, 2011.
Translation_EP1101506_Description_EuropeanPatent Office.pdf; Mehner et al; Jul. 3, 2002.
Translation_EP1101506_Claims_EuropeanPatent Office.pdf; Mehner et al; Jul. 3, 2002.
Espacenet—INPADOC patent family EP1101506.pdf.
"E-Z-EM Balloon Inflators Cat. No. 9529 [REF9529EU];" Merry X-Ray ; Product: 250422; retrieved on Nov. 14, 2013 from <http://orders.merryxray.com/webapp/wcs/stores/servlet/ProductDisplay?catalogId=11202&storeId=10051&productId=25341&langId=-1&parent_cateogry_rn=20280&lv10=19579&lv11=19737&lv12=&lvl3=>.
"E-Z-EM Flexi-Cuff silicone elastomer retention cuff;" Merry X-Ray ; Product: 263980; retrieved on Nov. 14, 2013 from <http://orders.merryxray.com/webapp/wcs/stores/servlet/ProductDisplay?catalogId=11202&storeId=10051&productId=25387&langId=-1&parent_cateogry_rn=20280&lv10=19579&lv11=19737&lv12=&lvl3=>.
"E-Z-EM Flexi-Tip;" Merry X-Ray—Product: 190005; retrieved on Nov. 14, 2013 from <http://orders.merryxray.com/webapp/wcs/stores/servlet/ProductDisplay?catalogId=11202&storeId=10051&productId=25345&langId=-1&parent_cateogry_rn=20280&lv10=19579&lv11=19737&lv12=&lvl3=>.
"E-Z-EM hard bulb or E-Z-EM E-Z-Flat device;" Merry X-Ray—Product: 292003; retrieved on Nov. 14, 2031 from <http://orders.merryxray.com/webapp/wcs/stores/servlet/ProductDisplay?catalogId=11202&storeId=10051&productId=25405&langId=-1&parent_cateogry_rn=101313&lv10=19579&lv11=19737&lv12=&lvl3=>.
International Search Report and Written Opinion of the Searching Authority for Application No. PCT/US05/46561; dated Sep. 13, 2007.
PROTOCO$_2$L™, Automated Carbon Dioxide Insufflation System for Virtual Colonoscopy; E-Z-EM; Virtual Colonoscopy; retrieved on Dec. 9, 2005 from <http://www.ezem.com/virtual_colon/proto.htm>.
"Enema Container for X-ray in Large Bowel—Enemaunit;" Horii Pharm. Ind., Ltd.; dated Oct. 1, 1977.
"Enemaunit—Disposable Implement for Intestinal Infusion upon X-ray Testing in Large Bowel;" Horii Pharm. Ind., Ltd.; dated Jul. 1998.
Office Action for U.S. Appl. No. 13/267,434 dated Nov. 8, 2013.
Notice of Allowance for U.S. Appl. No. 13/267,434 dated Feb. 19, 2014.
Office Action for U.S. Appl. No. 13/302,484 dated Oct. 21, 2015.
Office Action for U.S. Appl. No. 13/302,484 dated Apr. 9, 2015.
Notice of Allowance U.S. Appl. No. 13/302,484 dated Sep. 19, 2016.
Office Action for Canadian Application No. 2,702,489 dated Jun. 1, 2015.
Office Action for Mexican Application No. MX/a/2013/005850 dated Jun. 25, 2015.
Office Action for U.S. Appl. No. 14/459,365 dated Jun. 24, 2015.
Office Action for U.S. Appl. No. 13/402,455 dated Aug. 13, 2015.
Office Action for U.S. Appl. No. 13/402,455 dated Jan. 20, 2016.
Office Action for U.S. Appl. No. 13/302,484, dated Apr. 7, 2016, 16 pages.
Office Action for U.S. Appl. No. 14/459,365 dated Nov. 3, 2015.
Office Action for Canadian Application No. 2,818,844 dated Aug. 19, 2014.

Notice of Allowance for corresponding Chinese Application No. 201180056406.6 dated Jul. 2, 2015.
Notice of Allowance for corresponding Canadian Application No. 2,818,844 dated Jul. 14, 2015.
Notice of Allowance for corresponding Korean Application No. 10-2013-7016190 dated Jul. 31, 2015.
Notice of Allowance for corresponding Japanese Application No. 2013-541016 dated Sep. 8, 2015.
International Search Report and Written Opinion for Application No. PCT/US2011/061824 dated Feb. 9, 2012.
International Search Report and Written Opinion for Application No. PCT/US2013/032005 dated Jun. 18, 2013.
International Search Report and Written Opinion for Application No. PCT/US2006/041291 dated Sep. 13, 2007.
International Search Report for Application No. PCT/US2002/37384 dated May 19, 2003.
International Preliminary Search Report for Application No. PCT/US2008/079826 dated Apr. 20, 2010.
International Search Report and Written Opinion for Application No. PCT/US2008/079826 dated Apr. 20, 2009.
International Preliminary Search Report for Application No. PCT/US2008/083115 dated May 18, 2010.
International Search Report and Written Opinion for Application No. PCT/US2008/038115 dated Apr. 24, 2009.
Examiner's First Report on Australian Patent Application No. 2006306361 dated Sep. 6, 2011.
Examination Report for Australian Patent Application No. 2011331936 dated Jun. 24, 2014.
Canadian Office Action for Application No. 2,642,135 dated Mar. 24, 2010.
Office Action for Chinese Application No. 200680043998.7 dated Jan. 29, 2010.
Translation of Second Notification of Office Action for Chinese Application No. 200680043998.7 dated Jul. 14, 2010 (5 sheets).
Office Action for Chinese Application No. 200680043998.7 dated Oct. 27, 2010.
Office Action for Chinese Application No. 201180056406.6 dated Jul. 3, 2014.
Supplementary European Search Report for Application No. EP 02 78 9809 dated May 28, 2009.
Office Action for Application No. EP 02 789 809.7 dated Oct. 22, 2009.
Communication for European Application No. EP 02 789 809.7 dated Sep. 21, 2010.
Intention to Grant for EP Application No. 02 789 809.7 dated Apr. 27, 2011.
Supplementary European Search Report for Application No. EP 08 84 0766 dated Apr. 10, 2014.
Office Action for European Application No. EP 08 84 0766.3 dated Apr. 29, 2014.
Office Action for European Application No. 05 855 170.6 dated Jan. 31, 2011.
Office Action for Japanese Application No. 2008-537841 dated Mar. 30, 2012.
Office Action for Japanese Application No. 2008-537841 dated Oct. 2, 2012.
Office Action for Japanese Application No. 2013-541016 dated Jun. 3, 2014.
Office Action for Korean Application No. 10-2008-7012245 dated Jan. 30, 2012.
Office Action for Korean Application No. 10-2008-7012245 dated Sep. 21, 2012.
Office Action for Korean Application No. 10-2013-7016190 dated Jun. 27, 2014.
Office Action for U.S. Appl. No. 11/257,229 dated Apr. 16, 2008.
Office Action for U.S. Appl. No. 11/257,229 dated Sep. 25, 2008.
Office Action for U.S. Appl. No. 11/257,229 dated Mar. 10, 2009.
Office Action for U.S. Appl. No. 11/257,229 dated Sep. 1, 2009.
Notice of Allowance for U.S. Appl. No. 11/257,229 dated Jun. 17, 2010.
Office Action for U.S. Appl. No. 12/742,358 dated Mar. 20, 2012.
Office Action for U.S. Appl. No. 12/742,358 dated Aug. 2, 2012.
Office Action for U.S. Appl. No. 12/845,475 dated Jul. 27, 2011.

(56) References Cited

OTHER PUBLICATIONS

Notice of Allowance for U.S. Appl. No. 12/845,475 dated Dec. 23, 2011.
Office Action for U.S. Appl. No. 13/302,484 dated Dec. 30, 2013.
Office Action for U.S. Appl. No. 13/302,484 dated Jul. 29, 2014.
Office Action for U.S. Appl. No. 14/459,365 dated Sep. 17, 2014.
*Flow Orifices and Flow Restrictors Information | Engineering360*, [online] [retrieved Dec. 5, 2017]. Retrieved from the Internet: <URL: http://www.globalspec.com/learnmore/flow_control_fluid_transfer/pipe_tubing_hose_fittings_accessories/flow_orifices_flow_restrictors>. (2017) 2 pages.
*Special Section: Flow: Sizing orifice plates—ISA*, [online] [retrieved Dec. 5, 2017]. Retrieved from the Internet: <URL: https://www.isa.org/standards-and-publications/isa-publications/intech-magazine/2012/february/sizing-orifice-plates/>. (2012) 4 pages.
Office Action for European Application No. 14188116.9 dated Aug. 23, 2019.
Office Action for European Application No. 11 790 835.0 dated Oct. 14, 2015.

\* cited by examiner

DEVICE, SYSTEM, KIT OR METHOD FOR COLLECTING EFFLUENT FROM AN INDIVIDUAL

CROSS-REFERENCE

This application is a divisional of U.S. application Ser. No. 13/267,434, filed on Oct. 6, 2011, which is a divisional of U.S. application Ser. No. 12/029,159, filed Feb. 11, 2008, which is a continuation of U.S. application Ser. No. 10/497,625, filed Jun. 3, 2004, which claims priority from PCT/US02/37384, filed Nov. 21, 2002, which claims priority from U.S. Provisional Application Ser. No. 60/332,072, filed Nov. 21, 2001, each of which is incorporated herein by reference in their entirety.

FIELD OF THE INVENTION

The present invention relates to a device, method, system and kit for collecting effluent from an individual during or after a medical or diagnostic procedure. As used herein, the term "effluent" includes, but is not limited to, any solid, semi-solid, liquid, or gaseous matter from the inside of an individual's body. In an alternative embodiment, the present invention provides a means by which a desired medium can pass to and from a body cavity of an individual undergoing a medical or diagnostic procedure, and, at the same time, prevent the individual's effluent from coming into contact with the equipment used to perform the medical or diagnostic procedure. As used herein the term "medium", includes, but is not limited to, any solid, semi-solid, liquid or gaseous matter administered to an individual in order to perform a useful medical or diagnostic procedure.

BACKGROUND OF THE INVENTION

Current procedures for collecting effluent from an individual during a medical or diagnostic procedure pose various sanitation problems, among other problems. In many cases, the individual is not connected to an appropriate receptacle for collecting effluent during a procedure, permitting spillage, contamination, noise and stench of body fluids and gases to escape during or after the performance of the procedure. Also, it may be necessary for diagnostic purposes to observe the effluent of the individual, and to collect all or some of the expelled effluent during a procedure. This is often inconvenient or difficult when following presently known techniques.

For example, the diagnostic performance of gastrointestinal imaging, including but not limited to CT imaging, and others, is facilitated by distending a desired body part prior to and during the diagnostic procedure. Ideally, distention is maintained throughout the procedure to obtain the most accurate image. Currently, it is known to distend the colon or other body parts of an individual prior to and during examination by direct connection of an insufflator to the proximal end of a rectal catheter inserted into the rectum of the individual. With this device, air or $CO_2$, for example, is introduced into the colon. Due to cost prohibitions, however, insufflation equipment is used with multiple individuals. In this regard, it is essential that the equipment not be contaminated from use by any other patient. Frequently, effluent, such as stool, is expelled from the patient during the insufflation procedure, and often contacts and thus contaminates the insufflation equipment.

SUMMARY OF THE INVENTION

The above-mentioned disadvantages of the prior art are alleviated, in part, by the present invention. For instance, in one alternative embodiment, the present invention provides an effluent collection reservoir interfaced with a conduit used to administer a medium into an individual's body cavity during or after a medical or diagnostic procedure. Thus, any effluent expelled at the onset of a procedure migrates and collects in this reservoir, thereby preventing the effluent from impeding the administration of the medium. With the expelled effluent in the reservoir, the desired medium is free to migrate through the conduit and into the individual's cavity. In one alternative embodiment, the present invention is suitable for use with insufflation devices because it provides an efficient, disposable device by which a medium can pass to the patient while maintaining the sterility of the insufflator, such that it can be used with multiple individuals. In another embodiment, distention gas is free to flow bi-directionally, thereby allowing one to utilize the pressure-sensing capability of an electro-pneumatic insufflator, for example, which is used to distend a cavity (e.g., colon) automatically by a constant, user set pressure.

Also, in another embodiment of the present invention, a barrier is positioned in front of the connection site between the present invention and the equipment used to perform the medical or diagnostic procedure. Thus, effluent escaping from the reservoir cannot contact the equipment during the procedure. With barriers positioned in front of each opening to the effluent reservoir, the expelled stool/effluent can be easily contained to minimize mess and ease disposal of the effluent at the end of a procedure.

Therefore, it is an object of the present invention to provide a device, method, system and kit for collecting effluent from an individual.

It is a further object of the present invention to provide improvements in collecting effluent from an individual during or after a medical or diagnostic procedure, including, but not limited to, gastrointestinal imaging or endoscopy.

It is a further object of the invention to provide a means by which a medium can pass to and from an internal cavity of an individual undergoing a medical or diagnostic procedure, and at the same time, prevent effluent from the individual from contacting the equipment used in connection with the medical or diagnostic procedure.

It is a further object of the present invention to provide a disposable tubing device for use in conjunction with an insufflator mechanism to distend an anatomic segment of an individual in preparation for a medical or diagnostic procedure.

It is a further object of the present invention to provide a disposable tubing device capable of being used with a $CO_2$ insufflator device for distending an individual's colon in preparation for a gastrointestinal imaging procedure or endoscopic procedure.

Other objects, features, and advantages of the present invention will be apparent to those of ordinary skill in the art in view of the following detailed description of the invention and drawings.

BRIEF DESCRIPTION OF DRAWINGS

Corresponding reference characters indicate corresponding parts throughout the several views of drawings.

DETAILED DESCRIPTION OF THE INVENTION

Figure 1:
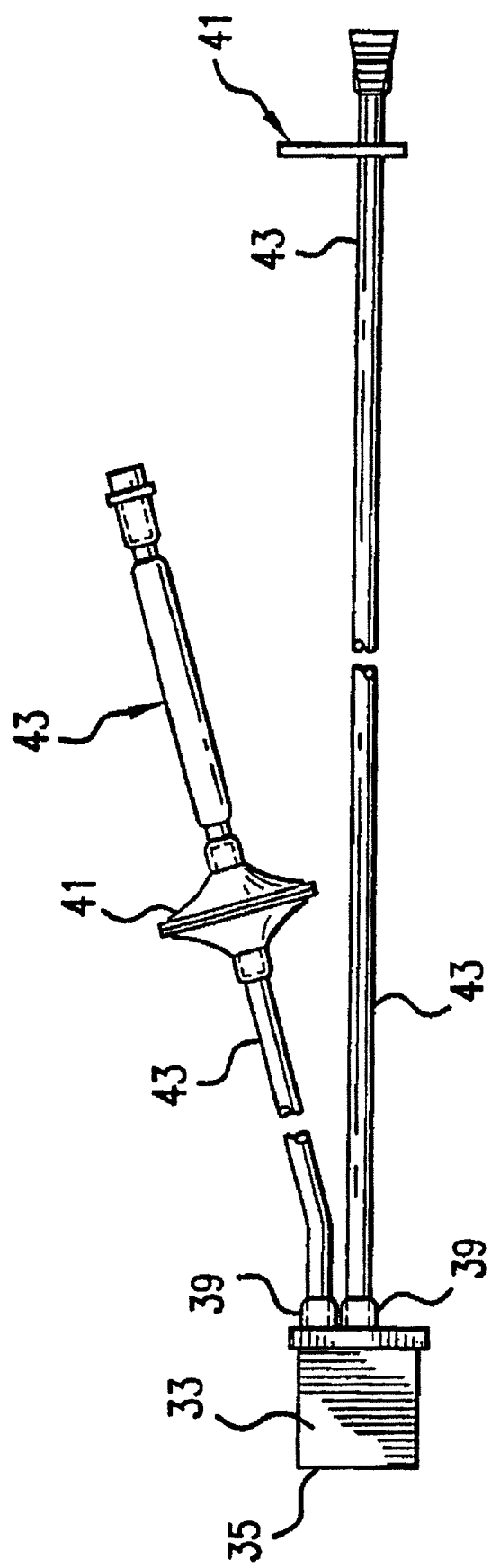
FIG. 1 shows an alternative embodiment of the present invention, without an insertable member.
Figure 2:
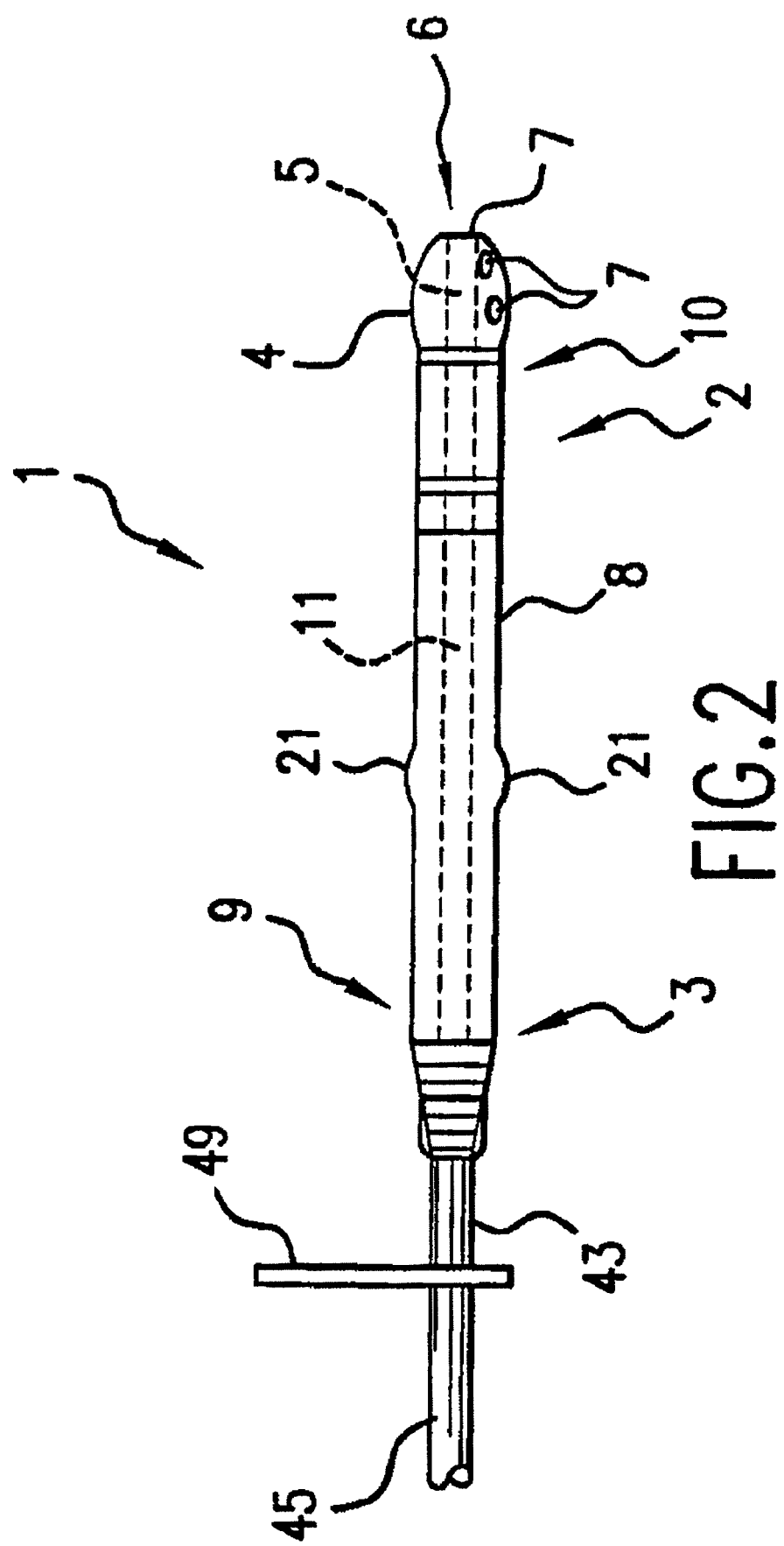
FIGS. 2-5 are perspective views of alternative effluent collection reservoirs of the present invention.
Figure 3:
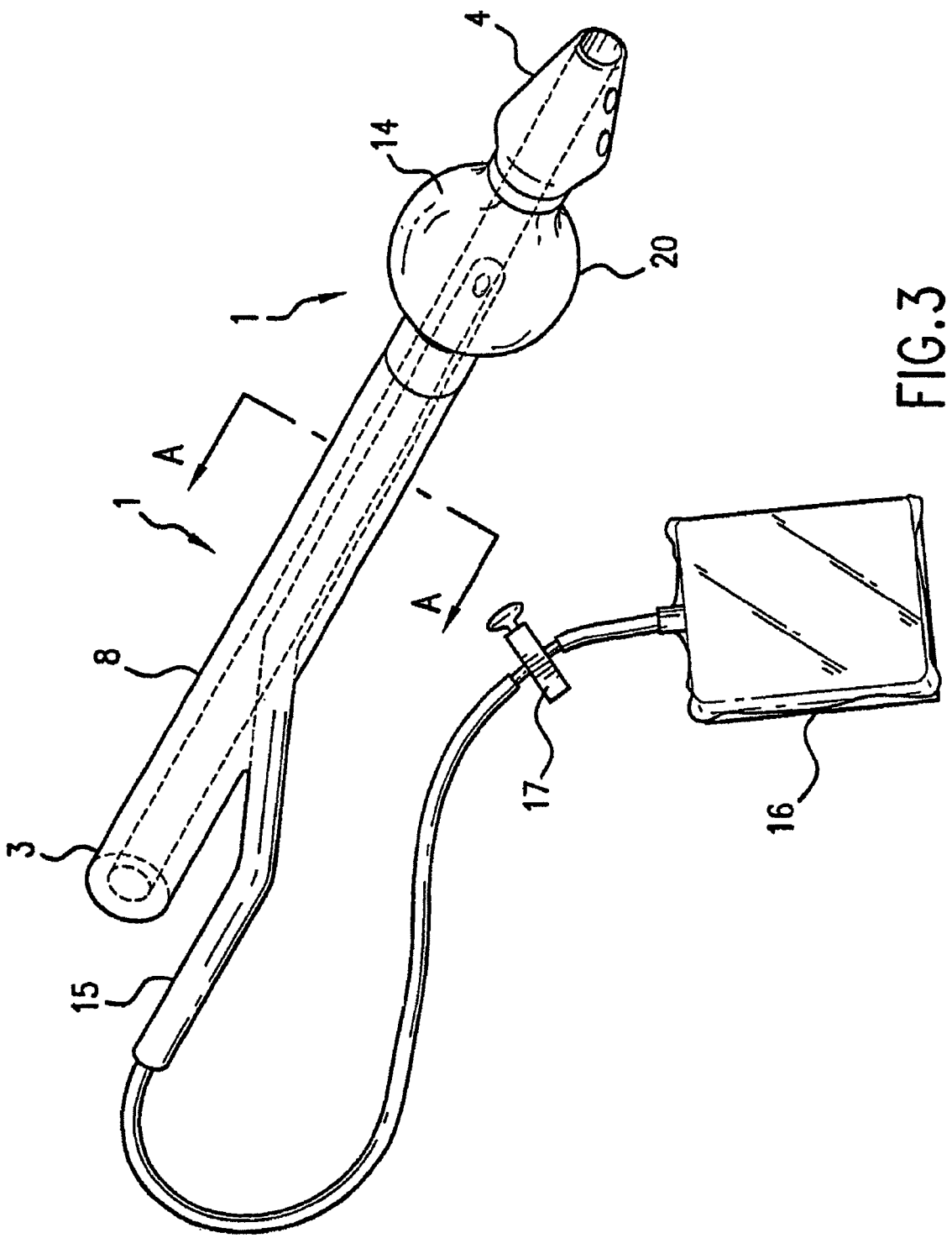
Figure 4:
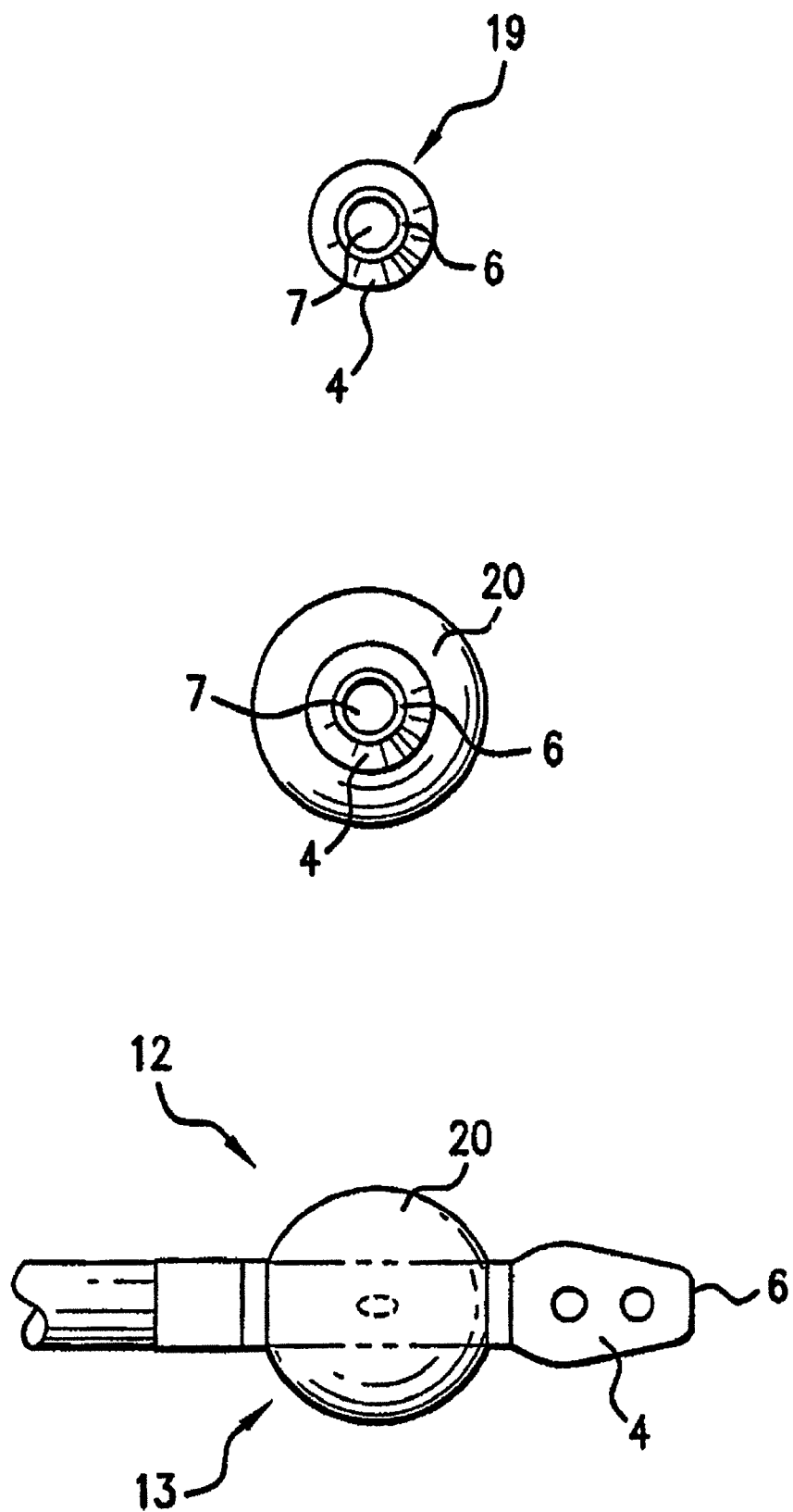
Figure 5:
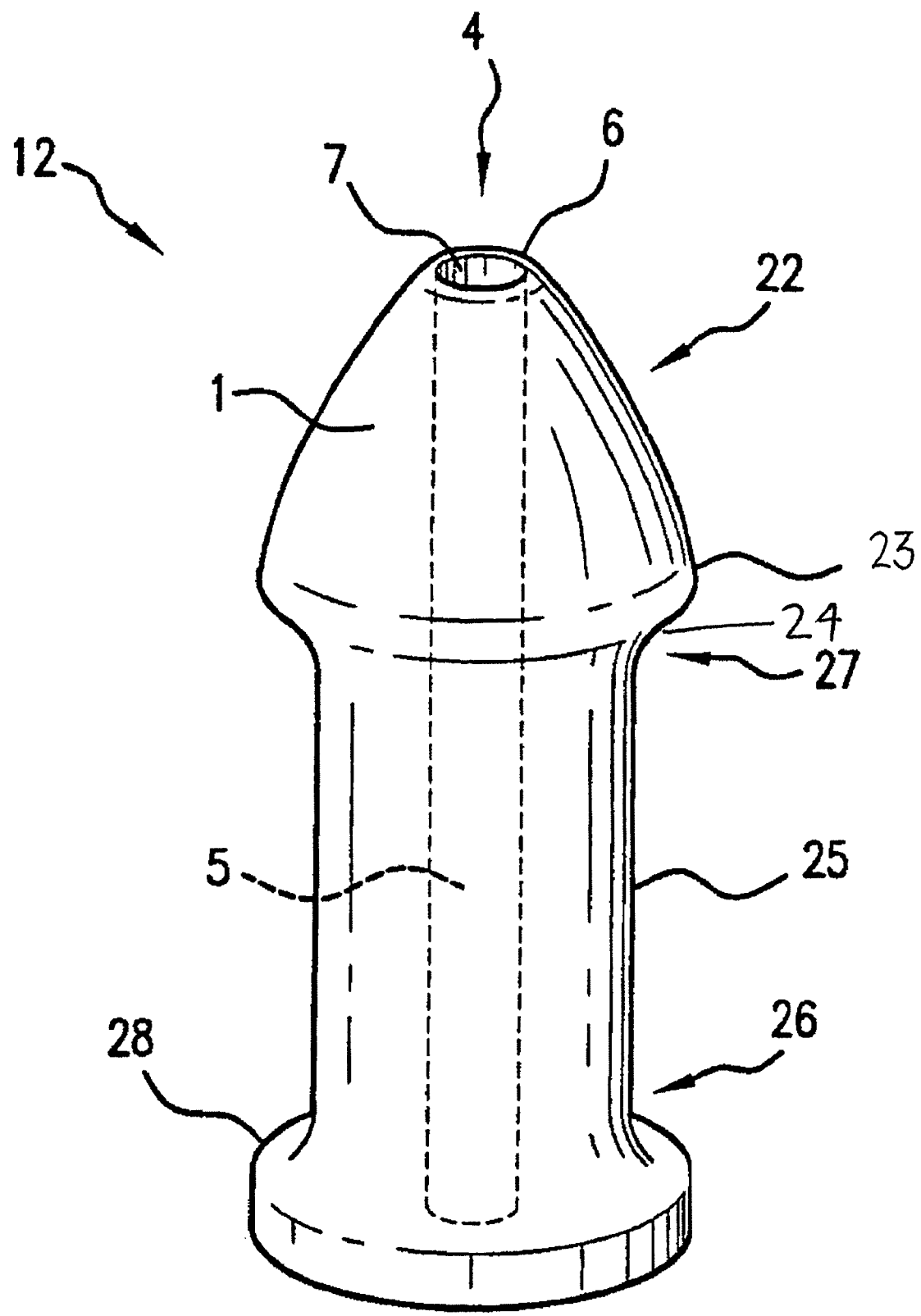
Figure 6:
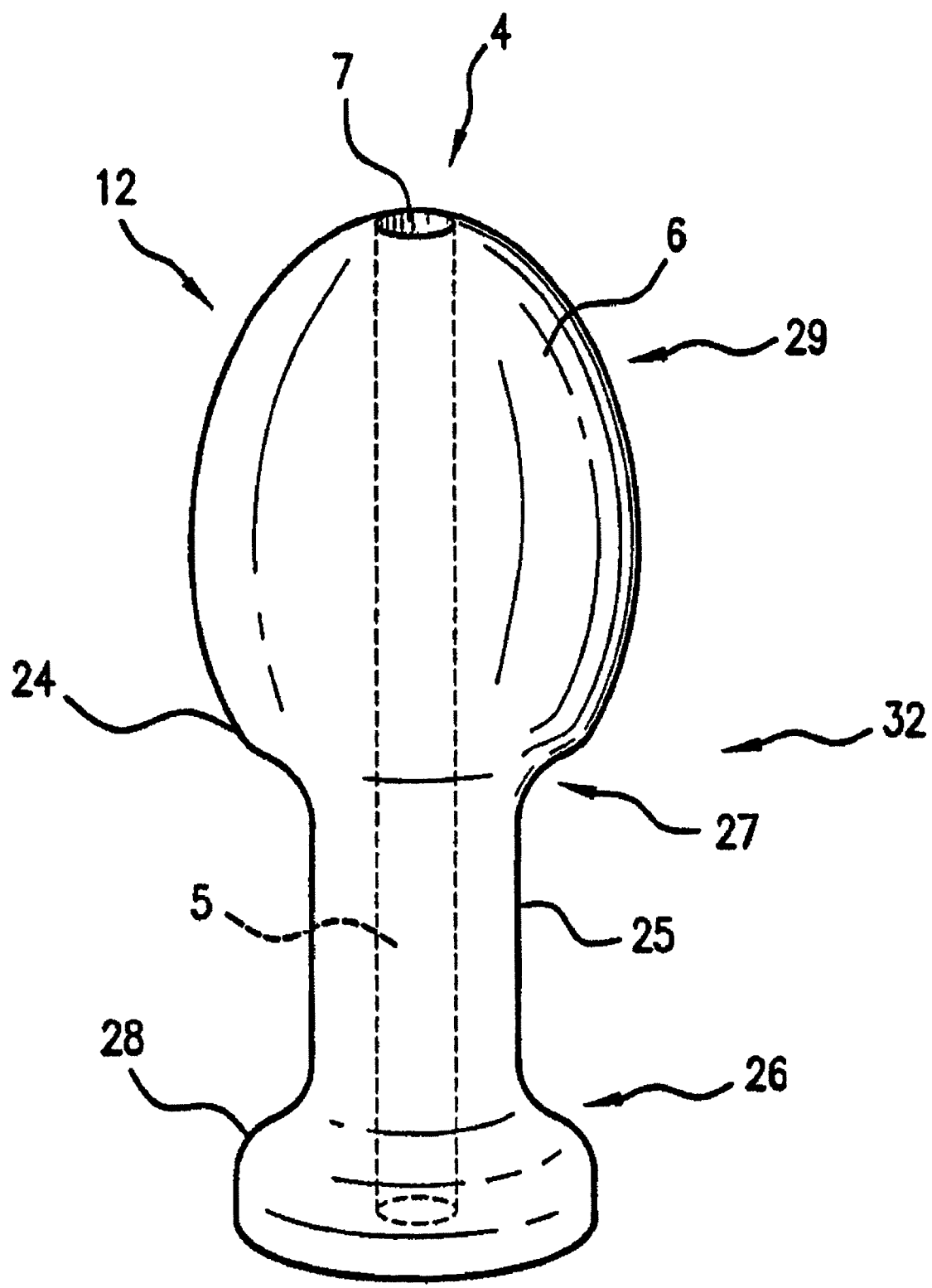
FIG. 6 is a side view of an alternative effluent barrier of the present invention.
Figure 7A:
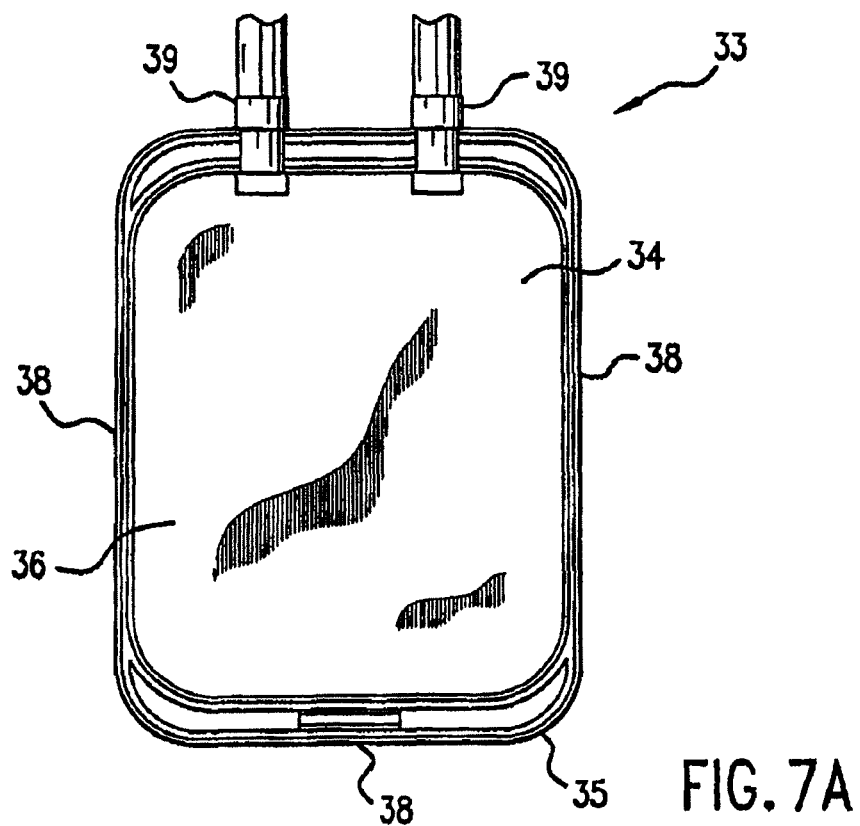
FIGS. 7A, 7B, and 8 are perspective views of alternative means for preventing the passage of effluent or medium from one location to another.
Figure 7B:
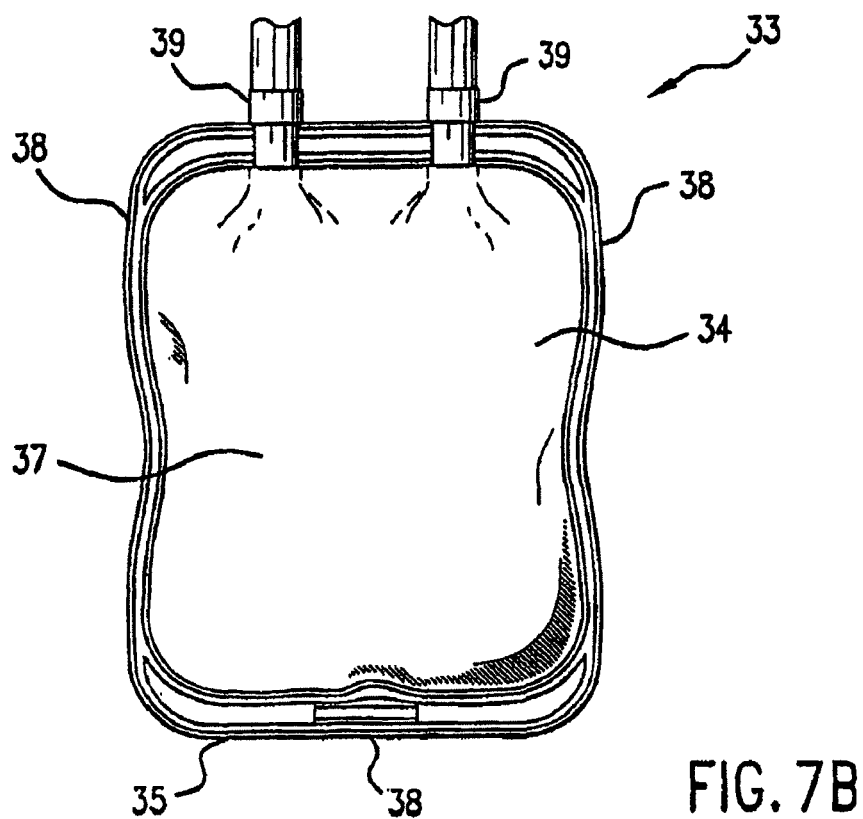
Figure 8:
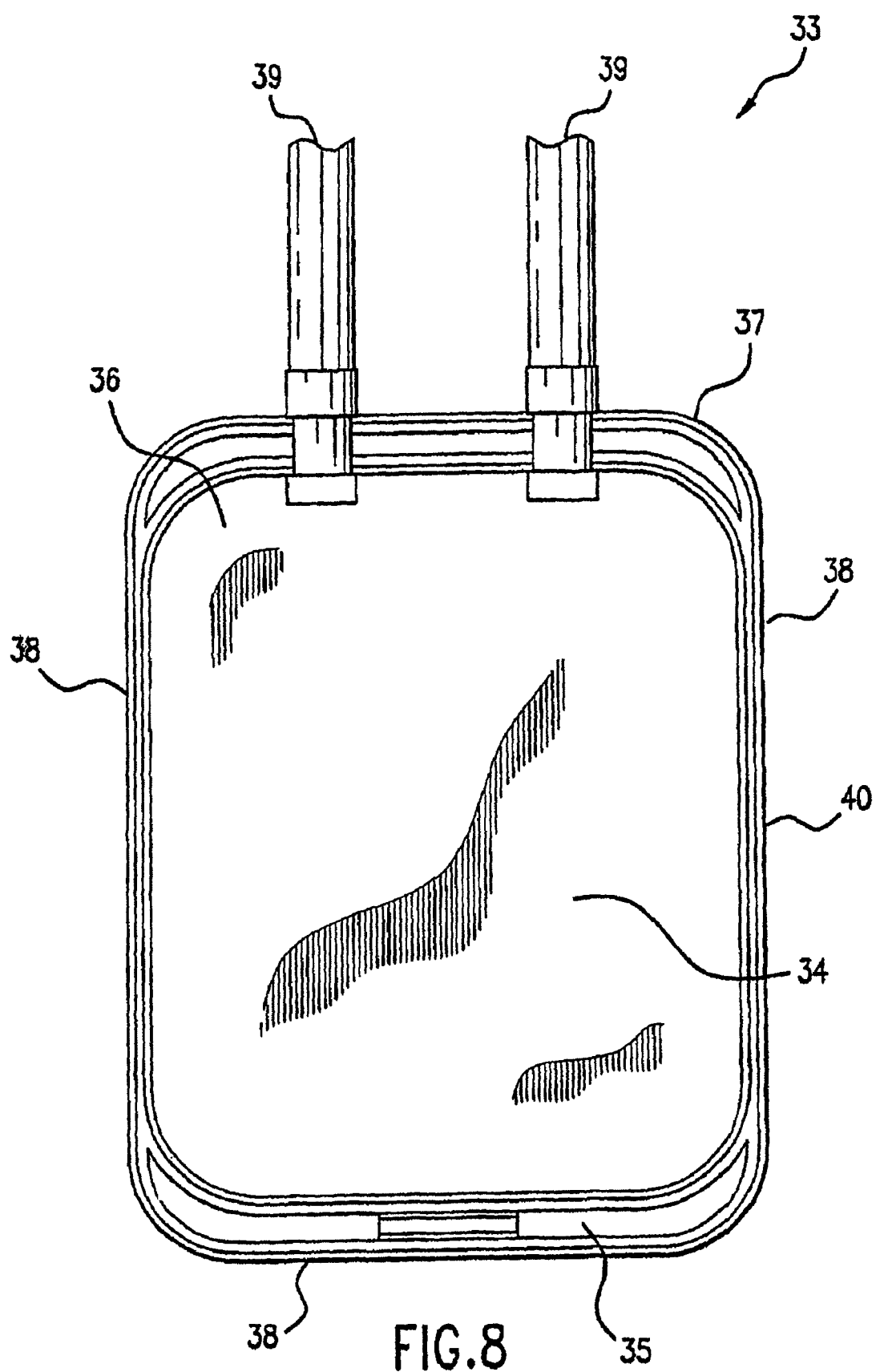
Figure 9:
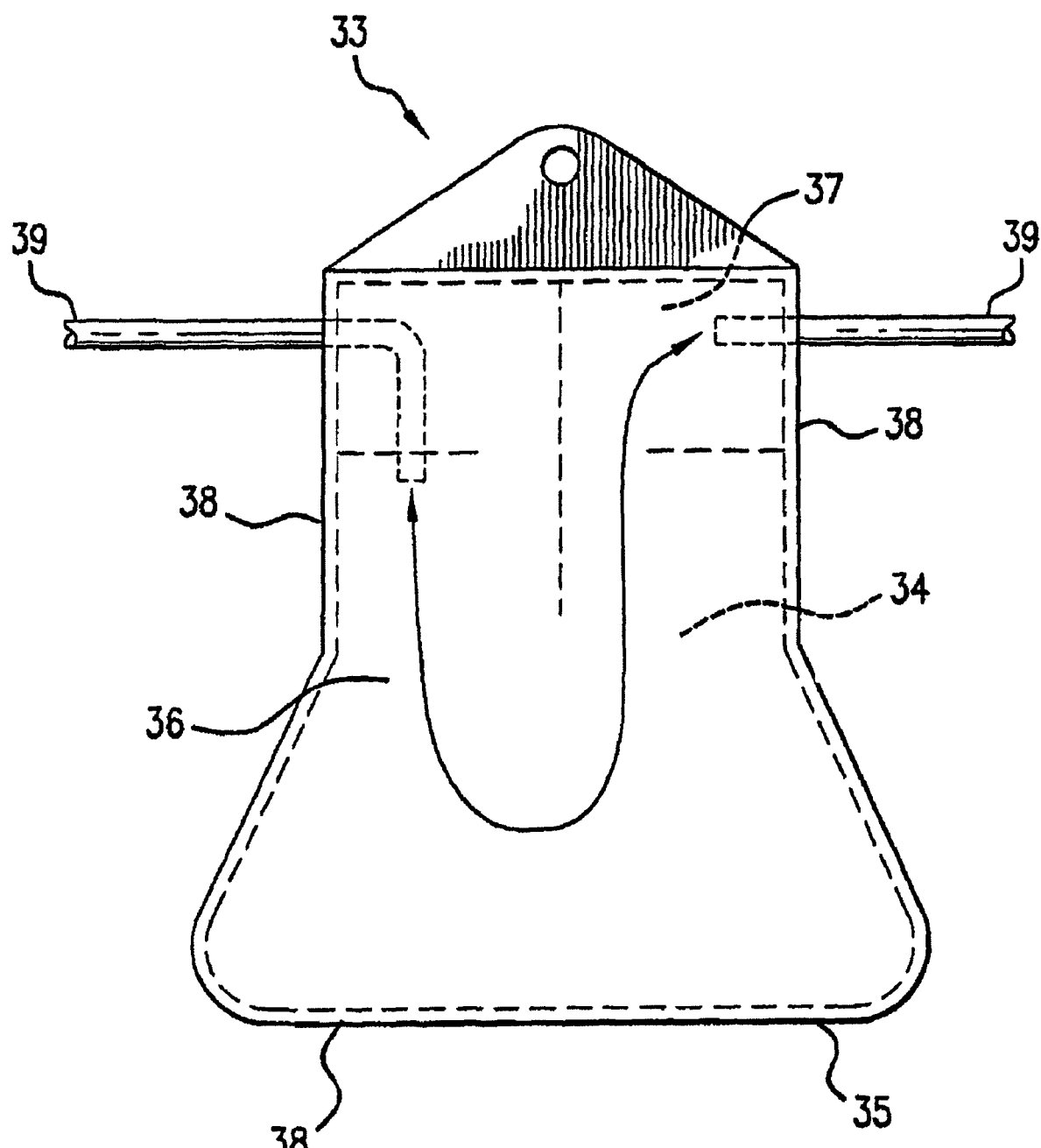
FIG. 9 is a perspective view of an alternative insertable member of the present invention.
Figure 10:
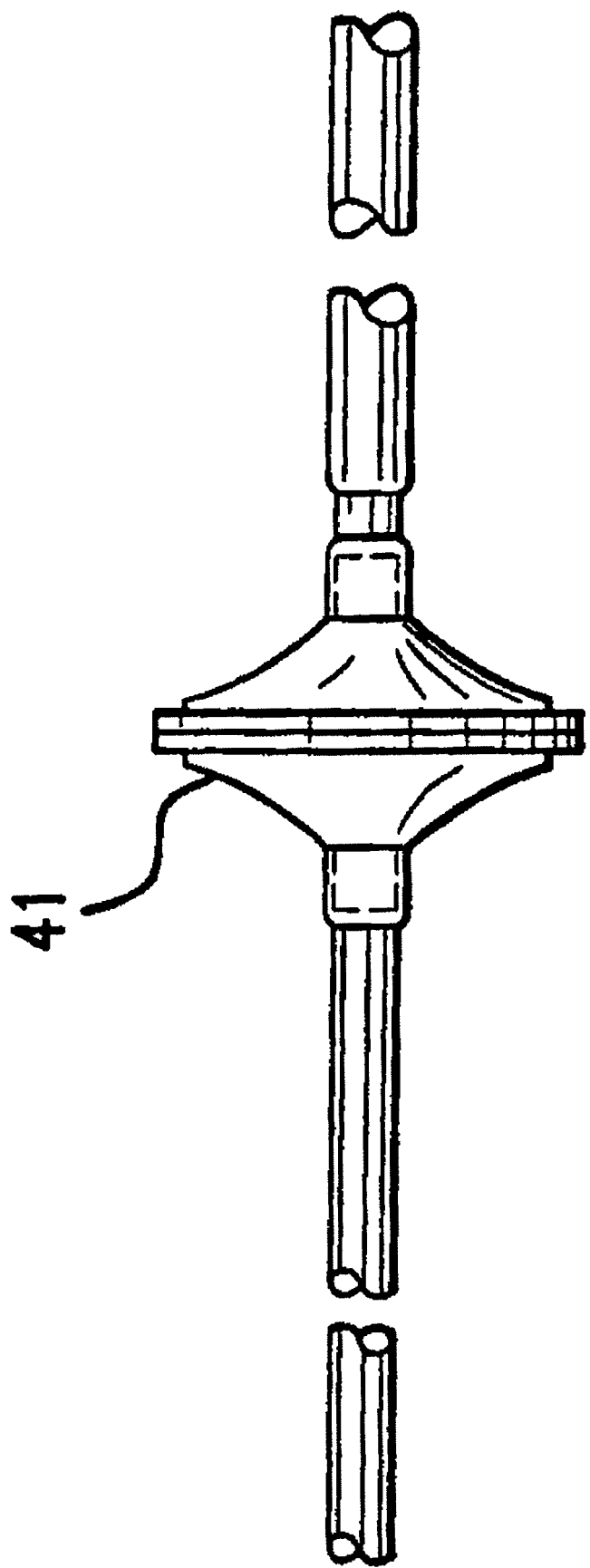
FIG. 10 is a perspective view of an alternative insertable member of the present invention, with enlarged expandable member.
Figure 11:
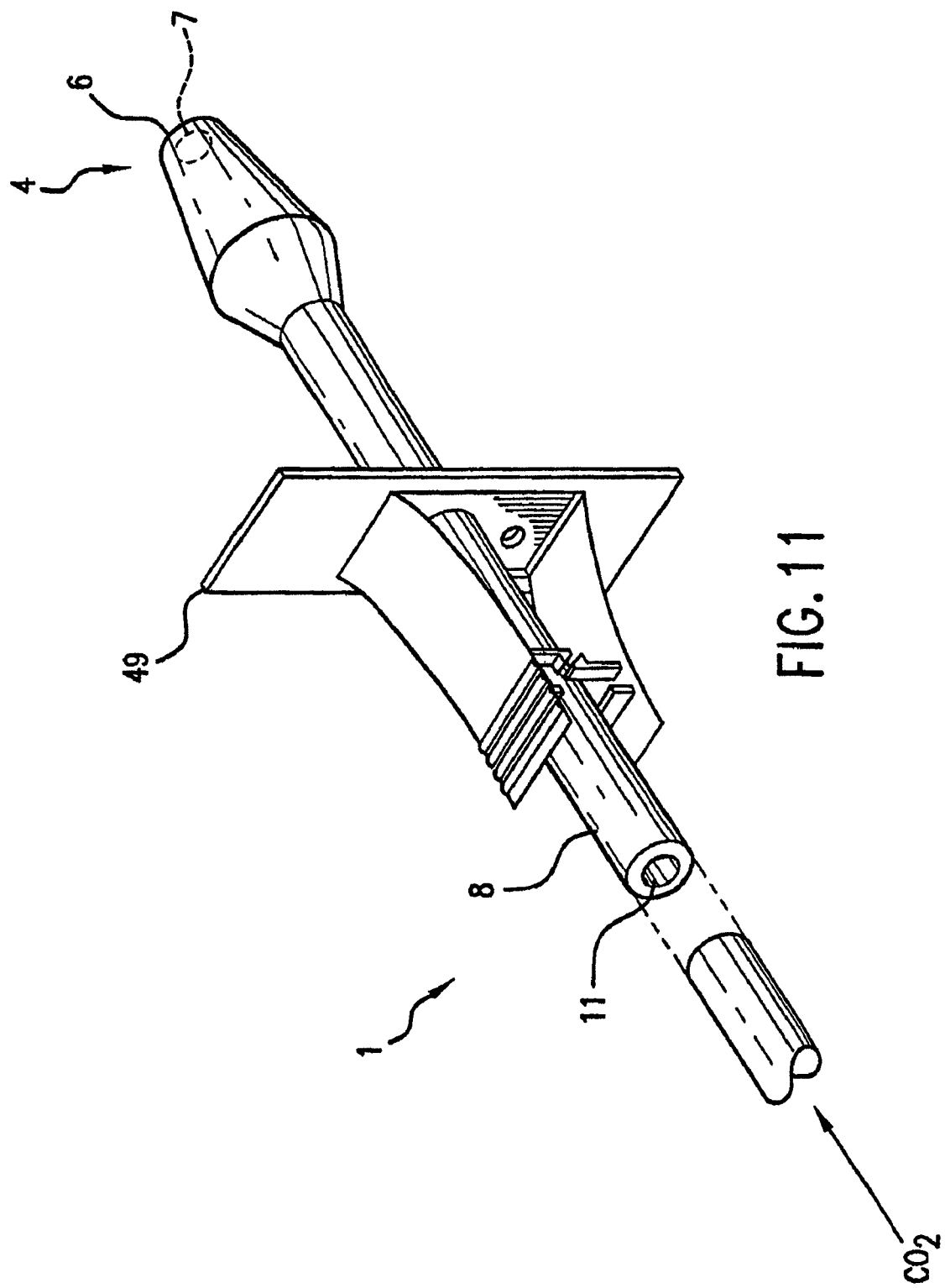
FIG. 11 is a front and side view of an alternative insertable member showing the expandable portion in non-enlarged and enlarged positions.
Figure 12:
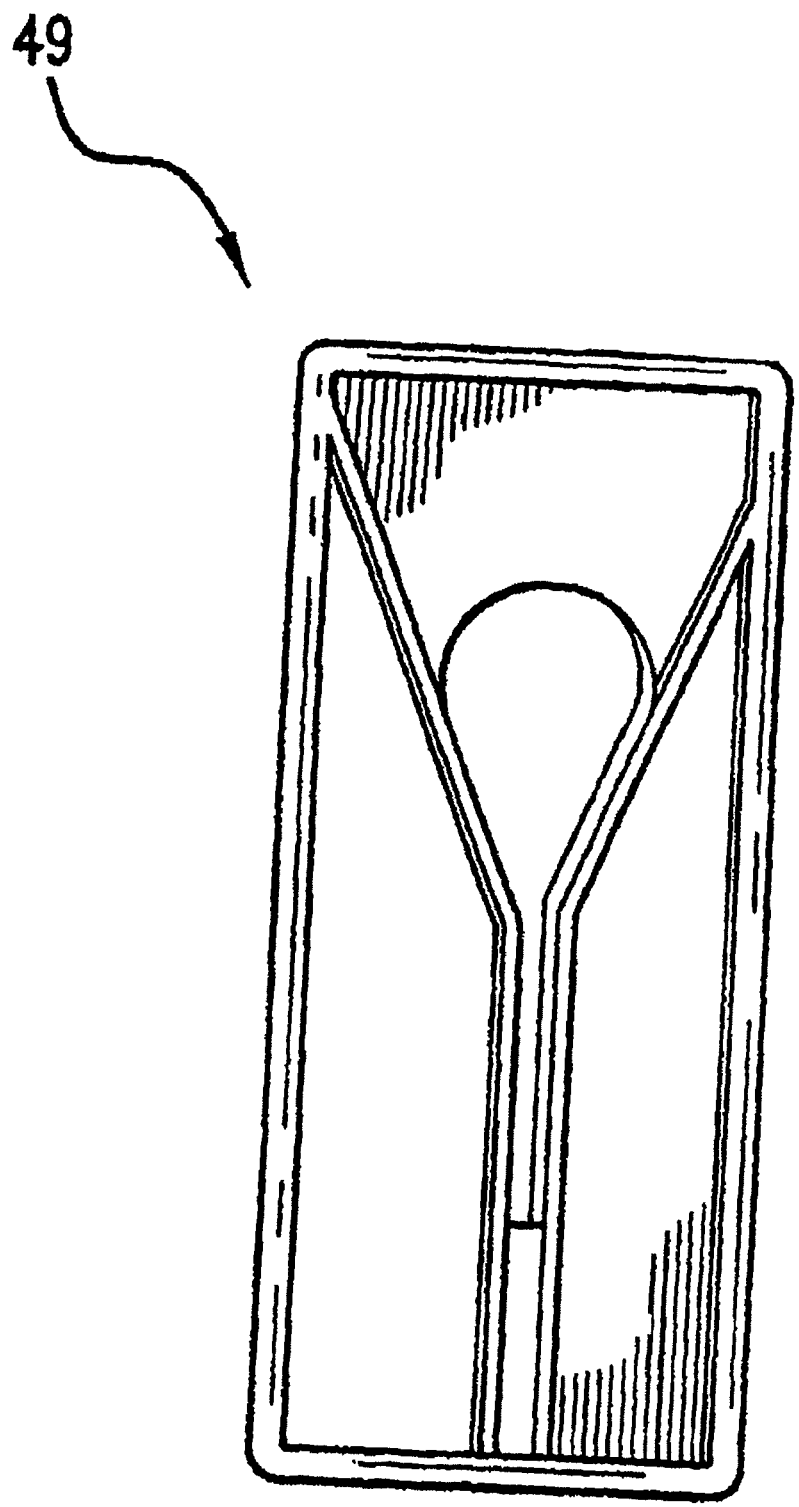
FIGS. 12 and 13 are perspective views of an alternative insertable member of the present invention.
Figure 13:
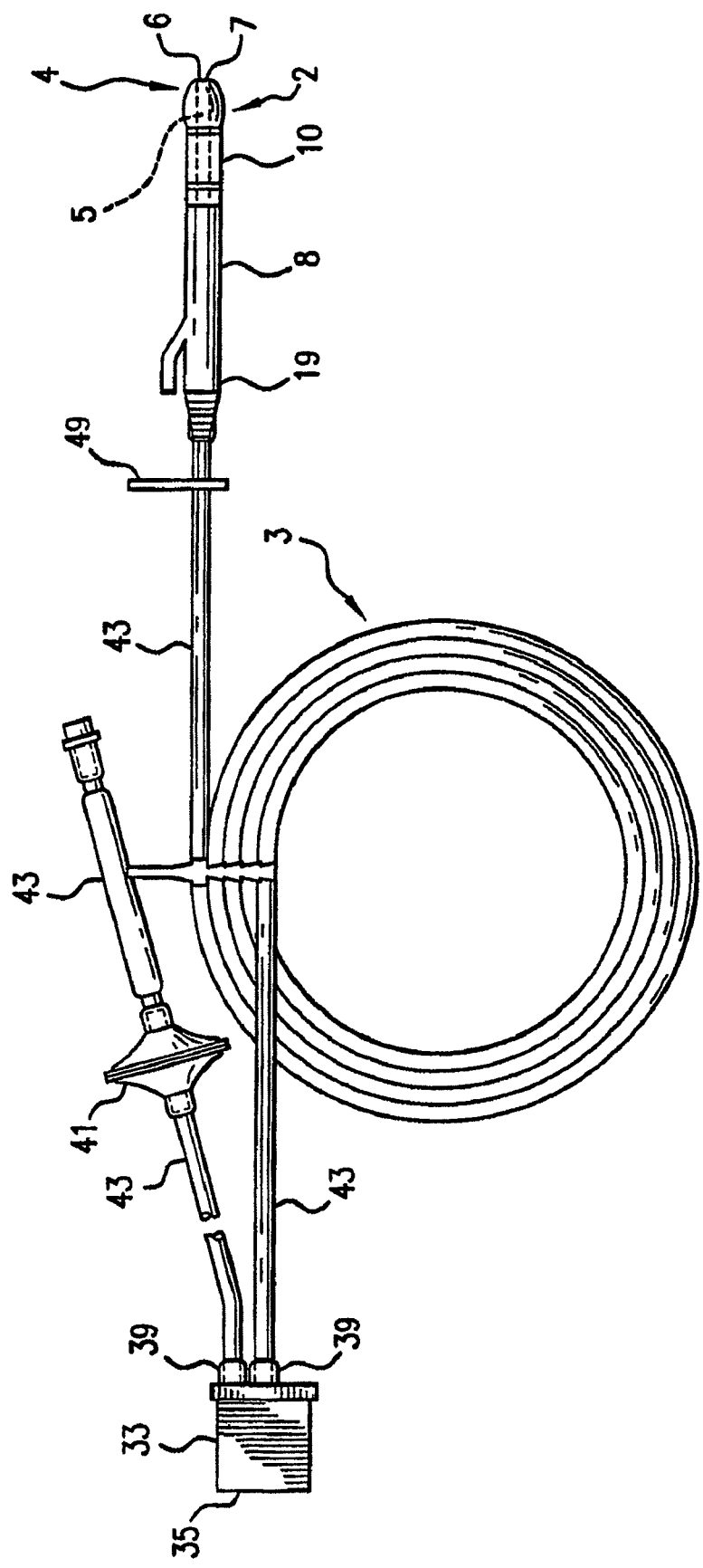
Figure 14:
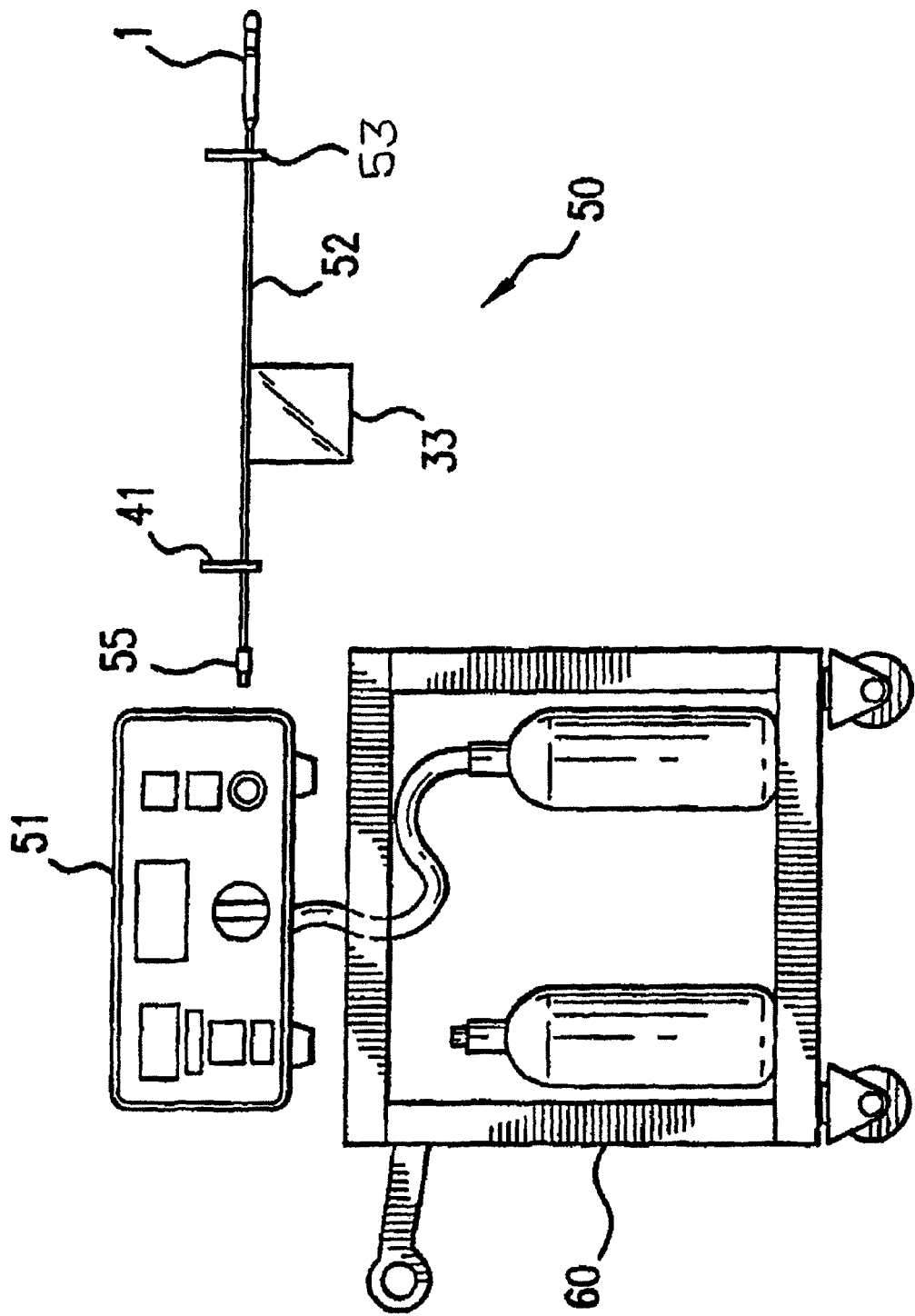
FIG. 14 shows alternative embodiment of the present invention, with insertable member connected thereto.

The device, system, kit or method of the present invention comprises an effluent reservoir. More specifically, the present invention comprises an effluent reservoir adapted for use in connection with performing a medical or diagnostic procedure of an anatomical area of interest. Such procedures may also include, but are not limited to, gastrointestinal imaging, including, but not limited to, X-ray imaging or virtual gastrointestinal imaging, for example. Virtual gastrointestinal imaging includes any technique of using computer software to view the inside of any section of the gastrointestinal tract, including CT imaging, MR imaging, PET imaging, PET imaging, or the like. Such medical or diagnostic procedures may also include fiberoptic endoscopy, optical colonoscopy, sigmoidoscopy and the like.

The effluent collection device comprising one or more means of interfacing with the device(s) used in the medical or diagnostic procedure, including, but not limited to an instrument for examining the interior of a body cavity, such as an endoscope, for example. Such device(s) may also include an insufflator or any other instrument for administering a powder, gas, liquid or vapor into a body cavity. Such device(s) may further include an aspirator or any other instrument that is used to create a partial or complete vacuum in a body cavity, or an instrument that removes liquids, solids or gases from a space by suction, particularly instruments used medicinally to evacuate a body cavity during or after a medical or diagnostic procedure.

The effluent reservoir interfaces with a medical or diagnostic device such that a medically and/or diagnostically useful procedure can be performed involving an individual's body cavity, and at the same time, prevent effluent passing through an opening of said cavity from impeding or otherwise adversely affecting the procedure or the outcome of the procedure. The effluent reservoir may also interface with the medical or diagnostic device(s) such that the effluent does not contact, and thus contaminate said device(s) during or after the medical or diagnostic procedure.

An Effluent Reservoir

In one alternative embodiment, the effluent reservoir may comprise a hollow interior capable of receiving and collecting effluent that passes through an opening of an individual's internal cavity during or after a diagnostic or medical procedure, for example. The effluent reservoir is particularly useful as a reservoir for collecting effluent from an individual's body cavity, thus preventing it from reentering the body cavity or contaminating a component, device or apparatus used in connection with a medical or diagnostic procedure.

In one embodiment, the effluent reservoir comprises an interior area having a closed bottom, and front and rear walls secured together around their periphery. The reservoir may also comprise one or more ports or openings for admitting or removing effluent to the interior of the effluent reservoir. The reservoir may further include one or more ports or opening for use in conveying a desired medium through the interior of the effluent reservoir. The reservoir may hold about 10 cc to 500 cc of fluid, preferably about 10 cc to 100 cc, more preferably about 60 cc to 100 cc. In one alternative embodiment, the effluent reservoir may hold approximately 60 cc or 100 cc of fluid, respectively.

In one alternative embodiment of the present invention, the effluent reservoir of the present invention has a bag-like shape. Alternatively, it may have a bottle-like, tray-like, box-like, or tube-like shape, for example. In another embodiment, the effluent reservoir may comprise a rigid container or jar, or it make take the form of a collapsible container. One advantage of a collapsible container is its smaller material volume which facilitates handling during manufacture, storage, shipping, use and disposal.

At least one opening of the effluent reservoir comprises a connection means. Such connection means includes, but is not limited to means for forming a connection with one or more other components. In one alternative embodiment, the connection means includes, but is not limited to, means for forming a Luer connection, Colder connection, barbed connection, male/female type connection or any equivalent thereof. In one alternative embodiment, the connection means provides means for forming a fluid-type seal between at least one effluent opening and one or more conduits, insertable members or apparatuses used in connection with a medical or diagnostic procedure.

The effluent reservoir of the present invention may be prepared from suitable plastic material whereby a strong, lightweight, reliable, yet economic container is provided. For example, the effluent reservoir of the present invention may be constructed of any suitable elastomeric material, such as olefin-based materials, including but not limited to, polyethylene, ethylene-propylene copolymers, ethylene-vinyl acetate copolymers, ethylene-acrylic ester copolymers, iononomers, and combinations thereof. Furthermore, film layers of polymers having gas barrier property, such as polyvinylidene chloride and ethylene-vinyl alcohol copolymers, as well as film layers of such polymers as polyvinyl chloride, polyester, polyamide and polyurethanes may also be used.

The effluent reservoirs may also comprise any flexible material, including polyethylene film, plasticized polyvinyl chloride film, plasticized polyvinylidene chloride film polyethylene/ethylene-vinyl acetate copolymer laminate, ethylene-vinyl acetate copolymer/polyvinylidene chloride/ethylene-vinyl acetate copolymer laminate, and polyethylene/ethylene-vinyl acetate copolymer/polyethylene chloride/ethylene-vinyl acetate copolymer/polyethylene laminate, among others. Also, the effluent reservoir may comprise materials that make it suitable for disposal in a flush toilet. Such materials comprising a biodegradable polymer, for example.

A Conduit

In the present invention, the effluent reservoir may be interfaced with one or more apparatus used to perform a medical or diagnostic procedure. Such interface may be achieved through one or more conduits positioned between the effluent reservoir and apparatus, for example. A conduit may include any hollow area capable of conveying any medium or effluent from one location to another. For example, in the present invention, the conduit may include a structure that comprises one or more hollow areas, and is capable of conveying a medium or effluent or otherwise functions as a passageway for those materials. The conduit may include, but is not limited to, a hollow cylinder such as a tube, channel, or pipe. The conduit may also comprise a single lumen or multilumens.

At least one portion of the conduit may comprise a connection means. Such connection means includes, but is not limited to, means for forming a connection with one or more components. In one alternative embodiment, the connection means includes a Luer connection, Colder connection, barbed connection, male/female connection or any equivalent thereof. In one alternative embodiment, the connection means provides means for forming a fluid-type seal between one or more portions of the conduit and an insertable member, opening of the effluent reservoir or one or more apparatuses used in the medical or diagnostic procedure.

The conduit of the present invention may be constituted of any suitable elastomeric material, such as olefin-based materials, including but not limited to, polyethylene, ethylene, ethylene-propylene copolymers, ethylene-vinyl acetate copolymers, ethylene-acrylic ester copolymers, Ionomers, and combinations thereof. Also, the conduits may be constructed of ployviylders chloride or ethylene-vinyl alcohol copolymers, as well as polyvinyl chloride, polyester, polyamide or polyurethanes, silicone, rubber, nylon, PTFE.

A Barrier for Controlling Flow of Effluent or Medium

The present invention may also comprise one or more bathers to prevent effluent or medium from migrating from one location to another. The one or more barriers may be positioned at one or more sites including, but not limited to, any location between the effluent reservoir and the area to be protected from contact with the individual's effluent. For example, one or more bathers may be so positioned in order to prevent effluent from contacting, and thus contaminating a component, device or apparatus used in connection with a medical or diagnostic procedure. Also, the barriers may be so positioned in various locations in order to prevent the medium or expelled effluent from migrating through the cavity opening and into the individual's internal cavity. In one alternative embodiment, the barrier may comprise one or more layers of material impervious to the passage of water, but not gas. Such a barrier may materially reduce the transfer of pathogens, such as viruses and bacteria, mucous and fluid. In one alternative embodiment, the effluent barrier may comprise a hydrophobic membrane to provide an anti-viral and anti-bacterial barrier, including but not limited to a 0.1 micron hydrophobic membrane.

The effluent barrier may also comprise any other well known, commercially available filtration media system impervious to biological matter. The filtration media's performance may be enhanced by placing an in-line check valve or unidirectional valve on a side of the filtration media. Additionally, the effluent barrier need not be an independent, stand-alone structure. It can form an integral part of any component of the present invention. For example, an appropriate hydrophobic membrane may form an integral part of the one or more openings of the effluent reservoir. The barrier may also form an integral part of the interior of the conduit or insertable member.

In another embodiment, the present invention may have an adjustable barrier for limiting or preventing the effluent or medium from migrating from one location to another during or after the medical or diagnostic procedure. The adjustable barrier may include but is not limited to, a clamp, valve, stop-cock, slide clamp or pinch clamp. In one alternative embodiment, the insertable member may support a locking pinch clamp.

An Insertable Member

Specifically, the insertable member is suitable for insertion into an opening of a cavity of an individual. The insertable member may have one or more hollow areas, such as a multilumen tube, for example. The body cavities of the individual may include, but are not limited to, the mouth, vagina, urethra, ear, nostril, uterus, appendix, cecum, hepatitic flexure, transverse colon, descending colon, sigmoid, rectum or any other body orifice, channel or opening to an individual's body, including incisions into the individual's body. The insertable member may include, but is not limited to, an instrument for examining the interior of the individual's cavity, such as a trocar, endoscope, enema tip, Foley catheter, entry needle, for example. It may also include an instrument for administering a powder, gas, liquid or vapor into a body cavity, such as an automatic or manual insufflator. The insertable member may further include an instrument for removing liquid, gas or solid from the interior of an individual's cavity.

The insertable member having a front portion and a rear portion, the rear portion having one or more connection means. Such connection means including, but is not limited to, means for forming a connection with one or more other components. In one alternative embodiment, the connection means includes, but is not limited to, means for forming a Luer connection, Colder connection, barbed connection, male/female type connection or any equivalent thereof. In one alternative embodiment, the connection means provides means for forming a fluid-type seal between a hollow area of an insertable member with one or more conduits or openings of the effluent reservoir.

The front portion comprising a tip structure supported thereon. The tip structure is adapted to initiate entry of the insertable member into an opening to an individual's body cavity. The insertable member may be structured so that part or at least substantially all of said member is inserted through the opening of the individual's cavity. In one alternative embodiment, the insertable member may have a hollow portion positioned internally. The hollow portion extending from the front end of the insertable member to its rear end. Thus, once inserted, the insertable member is capable of maintaining an opening to the cavity. For insertion into the body cavity, the tip may be lubricated and gently passed into the cavity. The tip can be removed from the cavity at any time by gentle traction therefrom.

The configuration of the tip structure may comprise various shapes and forms. For example, the tip structure may be cylindrical or non-cylindrical. The circumference of the tip structure may be substantially equal to or greater than other portions of the insertable member. The tip structure may also comprise an apex. The shape or form of one or more sections of the tip structure may include, but is not limited to, annular, planar, circular, rounded concave, convex, conical, elliptical, ellipsoidal, conidial, crescent-like, helical, oblong, oval, parabolic, round, sinusoidal, spherical, hemi-spherical, tapered, tubular, triangular, wedge-like, head-like or any other configuration capable of insertion into the opening of an individual's body cavity.

In another alternative embodiment, the insertable member may comprise a shaft having a distal end and proximal end. The tip structure may be positioned adjacent to the proximal end of the shaft. The distal end may be interfaced with the effluent reservoir. The interior of the shaft may comprise one or more hollow areas extending along part of or at least substantially the entire length of the shaft. The hollow area of the shaft can be completely or partially aligned with a hollow area of the tip structure of the insertable member, thus forming a conduit extending from the front portion of the insertable member to its rear portion. The tip and shaft may represent separate identifiable components or they may represent one single component of the insertable member.

In one embodiment, the insertable member may comprise a solid, substantially rigid material. Such materials may also include PVC or Polyethylene, for example. It may also comprise a substantially resilient material, such as rubber or an elastomeric polymer, such as a soft plastic, polyurethane, latex, nylon, PTFE, silicone or a blend thereof.

Restraining Means (e.g., Inflatable Cuff)

The present invention may also comprise one or more restraining means to maintain the insertable member in a desired position once inserted through the opening of the individual's body cavity. Also, the restraining means may prevent the tip of the insertable member from being displaced after insertion into the individual's body cavity. Further, the restraining means may prevent further penetration and/or maintain an appropriate seal between the insertable member and the outer periphery of the cavity once said member passes through the opening of the cavity. The restraining means may be selectively adjustable so that the insertion depth of the insertable member or its rotational orientation can be varied to fit different size anatomies.

In one alternative embodiment, the restraining means may comprise an expandable member adapted to facilitate placement of the insertable member in the individual's cavity. The expandable member may be positioned, in whole or in part, on the outer surface or within the insertable member. In another embodiment, the shaft or tip structure may be provided with an expandable member. In yet another alternative embodiment, the expandable member may be movable. For example, the expandable structure may be slidable along the shaft or tip structure. The expandable structure can be fixed on or selectively adjusted along the shaft or tip structure of the insertable member.

In one alternative embodiment, the expandable structure may take the form of an inflatable balloon-like structure supported on the shaft or tip structure of the insertable member. The expandable structure may be connected to an inflation conduit which extends into the interior of the insertable member. Here, the conduit may be provided with a stopcock or any other valve which can be connected to an inflation pump. In one embodiment, the conduit may comprise an inflation control stopcock and a connection for attaching the conduit to the nozzle of a suitable air pump, including, but not limited to, a syringe or other pump.

When the insertable member is inserted through the opening of a body cavity, the expandable structure supported on the shaft or tip structure can be inflated from its normal flat state into a distended balloon-like doughnut to prevent outward migration of the insertable member. The insertable member may be adjusted longitudinally along the shaft to adjust the depth into which the insertable member is inserted in the body cavity. When the appropriate depth of insertion and orientation has been achieved, the position of the insertable member may be maintained by inflating the expandable structure inside the body cavity, and preferably in the vicinity of the body cavity's opening. When inflated, the expandable member expands to a doughnut shape which is appropriate to accommodate the contour of the internal cavity, particularly the entry portion of the cavity.

In other embodiments, the present invention is a device for collecting effluent from an individual's body cavity through an opening of said cavity. Such device comprising an elongated hollow insertable member of solid non-inflatable construct having means defining an upper opening at an upper end of the insertable member and means defining a lower opening at the lower end of the insertable member. The insertable member having a hollow area of sufficient cross-section for the passage of effluent from the upper opening there through to the lower opening. The upper part of the insertable member being rounded and being insertable into the cavity opening. An annular expandable member is fixed to and encircles the upper part adjacent to the upper opening. The expandable member may be constructed to be expanded radially outwardly to circumferentially surround the insertable member in the vicinity of the upper opening to seal off the cavity opening such that effluent can escape from the cavity only through the hollow insertable member. The device including means for inflating the expandable member to expand it after it is positioned within the cavity opening. The spacing along the exterior of the insertable member between the expandable member and the lower end of the insertable member being such that after the upper part of the insertable member has been inserted into the cavity opening and the expandable member expanded, the cavity opening is compressed between the annular expandable member and the surface of the insertable member to seal the opening externally of the insertable member such that effluent material flows out only through the insertable member. The hollow insertable member including means at the lower end of the insertable member for securing an effluent reservoir to the lower end of the insertable member for passage of effluent out of the lower end and into the reservoir.

Abutment

The restraining means may also include an abutment positioned on the insertable member. For example, the restraining means may comprise an insertable member positionable in or near the opening to an individual's body cavity (e.g., anal sphincter) for support therein by one or more abutment surfaces. In one embodiment, the tip structure of the insertable member has a generally cone-shape configuration. The base of the cone forming a first radial abutment surface. The apex of the cone is used to initiate entry of the insertable member into the opening of the individual's body cavity. The tip structure also comprises a central section having a distal end and proximal end. The proximal end of the central section is positioned adjacent to the base of the cone. The proximal end of the central section has a diameter less than that of the base of the cone. The distal end of the central section has a diameter greater than that of its proximal end, forming a second radial abutment surface. Once inserted, the opening portion of the cavity is positioned between the first and second radial abutment surfaces.

The restraining means may also comprise a cylindrical head, having a first circumference along an axis. The insertable member also comprises a central section near or adjacent to the base of the cylindrical head. The central section having a proximal end and a distal end. Said distal section having a generally cone-shaped configuration, thus providing a generally planar radial first abutment surface. There is also a second abutment surface adjacent to the proximal end of the central first section.

In the Figures, alternative embodiments of the present invention are shown, particularly a device method, system and kit for receiving effluent from an individual. More specifically, the present invention comprises an effluent reservoir (33). The interior (47) of the reservoir (33) may comprise a hollow area (34) capable of receiving and collecting effluent that passes from an individual's internal cavity through the insertable member (1) during or after a diagnostic or medical procedure, for example.

In one embodiment, the effluent reservoir (33) comprises a hollow area (34) having a closed bottom (35), and front and rear walls (36, 37) secured together around their periphery (38). The reservoir (33) may also comprise one or more ports (39) for admitting or removing effluent to the interior of the effluent reservoir. The reservoir (33) may further include one or more ports (39) for use in conveying a medium to or from the interior (34) of the effluent reservoir (33). In one alternative embodiment, the effluent reservoir (33) make take the form of a collapsible container. In another embodiment, the effluent reservoir may comprise a rigid container (48), or it make take the form of a collapsible container.

The present invention may also comprise one or more barriers (41). The one or more barriers (41) may be positioned at one or more sites including, but not limited to, any location between the effluent reservoir (33) and the area to be protected from contacting the individual's effluent. For example, one or more barriers (41) may be positioned in order to prevent effluent from contacting, and thus contaminating a component, device or apparatus used in connection with a medical or diagnostic procedure. Also, the one or more barriers (41) may be positioned in various locations in order to prevent the effluent or medium migrating from the effluent reservoir (33) through the insertable member (1) and into the individual's internal cavity. In one alternative embodiment, the barrier (41) may comprise one or more layers of material impervious to the passage of water, but not gas. Such a barrier may materially reduce the transfer of pathogens, such as viruses and bacteria, mucous and fluid. In one alternative embodiment, the effluent barrier (41) may comprise a hydrophobic membrane to provide an anti-viral and anti-bacterial barrier, including but not limited to a 0.1 micron hydrophobic membrane. In another embodiment, the adjustable barrier may include a clamp, valve, stop-cock, locking pinch clamp (49).

In the present invention, the effluent reservoir (33) or desired medical equipment may be engaged with one or more conduits (43). A conduit may include a hollow area (45) capable of conveying any medium or effluent from one location to another. The invention may also comprise an insertable member. In one alternative embodiment of the present invention, insertable member (1) may have a front portion (2) and a rear portion (3). The front portion having a tip structure (4) supported on the insertable member (1). The tip structure is suitable for initiating entry of the insertable member (1) into an opening to an individual's body cavity. The apex of the tip structure (6) having one or more openings (7). The one or more openings may be interfaced with at least one hollow area (5) positioned in the interior of apex (6). The hollow area (5) may extend along the length of the tip structure (4). The tip structure (4) may comprise multiple openings each interfaced with a hollow area (5) positioned inside the tip structure (4). The insertable member (1) may comprise shaft (8) having a distal end (9) and proximal end (10). The tip structure (4) may be positioned at or near the proximal end of the shaft (10). The interior of the shaft (8) may comprise one or more hollow area (11). One or more hollow areas may extend along the length of the shaft (8). The hollow area (11) of the shaft (8) can be aligned with the hollow area (5) of the tip structure (4), thus forming a channel extending from the front portion of the insertable member (2) to its rear portion (3). The insertable member (1) may comprise means for fastening said member to one or more conduits (43) leading to an effluent reservoir (33), or medical apparatus or any component thereof.

The insertable member of the present invention may also comprise one or more restraining means (12). The restraining means may comprise an expandable structure (13). In one embodiment, the shaft (8) or tip structure (4) may be provided with an expandable structure (13). In one alternative embodiment, the expandable structure (13) may take the form of an inflatable balloon-like structure (14) supported on the shaft (8) or tip structure (4) of the insertable member (1). The balloon-like structure (14) may be connected to an inflation conduit (15) which may be positioned in the interior or exterior of the insertable member (1). The inflation conduit (15) may be interfaced with an inflation pump (16) such that a gas or liquid can be pumped through the conduit (15) and in the balloon-like structure. Also, the inflation conduit (15) may be interfaced with a stopcock, valve, clamp or any other means for preventing or allowing the flow of gas or liquid from escaping or passing through the inflation conduit (15). In one embodiment, conduit (15) may comprise an inflation control stopcock (17) and a means for attaching the inflation conduit (15) to the nozzle of inflation pump (16). In one embodiment, expandable structure (13) is an E-Z-EM Flexi-Cuff® silicone elastomer retention cuff, or a similar device. This product is sold by E-Z-EM, Inc., Westbury, N.Y.

When the insertable member (1) is inserted through the opening of a body cavity, the balloon-like structure (14) supported on the shaft (8) or tip structure (4) can be inflated from its normal flat state (19) into a distended balloon-like doughnut (20) to prevent undesirable movement of the insertable member (1).

The restraining means (12) may also include an abutment positioned on or in the vicinity of the insertable member (1). For example, the restraining means (12) may comprise an insertable member (1) positionable in or near the opening to an individual's body cavity (e.g., anal sphincter) for support therein by one or more abutment surfaces. In one embodiment, the tip structure (6) of the insertable member (1) has a generally cone-shape configuration (22) The base of the cone (23) forming a first radial abutment surface (24). The apex (6) of the tip structure (4) is used to initiate entry of the insertable member (1) into the opening of the individual's body cavity. The insertable member (1) also comprises a central section (25) having a distal end (26) and proximal end (27). The proximal end (27) of the central section (25) is positioned adjacent to the base of the cone (23). The proximal end (27) of the central section (25) has a diameter less than that of the base of the cone (23). The distal end (26) of the central section (25) may have a diameter greater than that of its proximal end (27), thus forming a second radial abutment surface. Once inserted, the orifice, or the periphery thereof, of the cavity is positioned between the first and second radial abutment surfaces (24, 28) to secure the insertable member (1) inside the individual's body cavity.

The restraining means (12) may also comprise a cylindrical head (29) having a first circumference along an axis.

The insertable member (1) also comprises a central section (25) having a distal section (26). It also has a proximal section (27) having a generally cone-shaped configuration (32), thus providing a generally planar radial first abutment surface (24) at or near the proximal section (27). There is also a second abutment surface (28) adjacent to the distal end (26) of the central section (25).

Referring to FIGS. 14-17, a disposable device for use with an insufflator apparatus or unit is shown. The device (50) is for use with an automatic insufflation unit (51). An insufflation unit suitable for use with the tubing device of the present invention includes, but is not limited to, the E-Z-EM PROTOCO$_2$L774™ Colon Insufflator or a similar device. This product is sold by E-Z-EM, Inc., Westbury, N.Y. When device (50) is used with an insufflation unit (51), such device (50) prevents contamination of the unit by any effluent discharged by the individual through the rectum. In one embodiment, device (50) is supplied in sterile form. In another embodiment, one or more components of the present invention is provided in latex-free form. Device (50) may be suitable for use with a single patient.

Device (50) provides tube (52). Tube (52) may include, but is not limited to, a flexible tube comprising vinyl or a similar plastic. Device (50) also includes a single lumen insertable member (1) located at the distal end of tube (52). Insertable member (1) is insertable into an individual's rectum. In one embodiment, the single lumen insertable member is E-Z-EM Catalog No. 8816, E-Z-EM Flexi-Tip®, or any equivalent thereof. This product is also sold by E-Z-EM of Westbury, N.Y. In another embodiment, tip structure (4) is a dip molded vinyl tip. The molded vinyl tip may be integrally connected to a locking pinch clamp (49).

Clamp (53) is located on tubing (52) proximally to insertable member (1). In one embodiment, clamp (53) is a slide clamp attached to tubing (52). Clamp (53) may be used alone or in conjunction with effluent reservoir (33) to collect any expelled stool/effluent from the individual during or after the duration of the procedure. At the end of the procedure, by actuating clamp (53), the expelled stool/affluent is contained inside effluent reservoir (33) to minimize mess and ease disposal of the effluent.

Effluent reservoir (33) is used to retain stool/effluent expelled by the patient during the insufflation procedure. Effluent reservoir (33) may be located proximally to clamp (53). In one embodiment, effluent reservoir (33) is a flexible container, preferably a collapsible polyvinyl bag. Effluent reservoir (33) is directly in-line with $CO_2$ gas flow through tubing (52). Because effluent reservoir (33) is directly in-line with the insufflation gas flow through tubing (52), any residual stool expelled at the onset of the procedure migrates and collects in this reservoir (33), thereby preventing a large column of effluent from blocking passage of the insufflation gas during the procedure. With the expelled stool in the effluent reservoir (33), gas from a pneumatic electro-pneumatic insufflator or manual insufflator is free to migrate to the patient through tubing (52). Additionally, distention gas is free to flow bi-directionally, thereby allowing one to utilize the pressure-sensing capability of the electro-pneumatic insufflator. This permits the colon to be distended automatically by a constant, user-set pressure.

In an embodiment, effluent reservoir (33) includes container (40). Container (40) may comprise, for example, a flexible plastic such as vinyl such that the bag is flexible and collapsible. Container (40) having a volume including, but is not limited to, about 20 cc to about 150 cc, or 80 cc, 60 cc, or 120 cc or 140 cc. Effluent reservoir (33) also includes two tubing connection ports (39) and (39) integral to its top surface. In one embodiment, connection ports (39) are commercially available Colder locking medical tubing connections, or similar devices. In an alternative embodiment, container (40) comprises a rigid container, such as a plastic vial. The primary advantage of a flexible bag over a rigid container, however, is the bag's smaller material volume that needs to be handled during manufacture, storage, shipping, use and subsequent post-procedure disposal.

In one embodiment, effluent reservoir (33) is kept at or below the level of the patient during the diagnostic procedure. Alternatively, effluent reservoir (33) may be elevated above the level of the patient while the patient is still attached to the device. Under these circumstances, it might be beneficial to completely close slide clamp (53) to prevent effluent/stool from reentering the individual's cavity through the insertable member.

Barrier (41) is located in-line on tubing (52). Barrier (41) may be located adjacent or proximally to effluent reservoir (33). In one embodiment, the barrier may be a filter. Filters suitable for use herein include, but are not limited to, any filter suitable for providing an anti-viral and anti-bacterial barrier to prevent contamination of the insufflation apparatus. In one embodiment, barrier (41) is a hydrophobic filter, especially a 0.1-micron hydrophobic membrane. By utilizing a hydrophobic filter proximal to effluent reservoir (33), any viral and/or bacterial matter expelled from the patient is contained in the reservoir (33) for the duration of the procedure.

Tubing set (52) attaches at connection (55) to an insufflator. In one embodiment, connection (55) is a commercially available Colder locking medical tubing connection, or a similar device. In one embodiment, tubing (52) is connected to an automatic $CO_2$ gas insufflator.

Insertable member (1) includes expandable structure (13) for maintaining the level of colonic distention during the diagnostic procedure. When inflated, expandable structure (13) prevents gas from escaping during the diagnostic procedure. This represents an improvement over the currently used hand bulb distention method, because gas can leak from the rectal cavity during the diagnostic procedure. A balloon suitable for use in herein includes, but is not limited to, E-Z-EM Balloon Inflators Cat. No. 9529 [REF 9529EU]. In one embodiment, expandable structure (13) is inflated about 1 cc to about 100 cc with air.

In one embodiment, cart (60) is designed to accommodate the human factors associated with the environment in which the present invention is used. Its primary functions are support of the insufflator unit and $CO_2$ supply cylinders on a mobile platform within the CT or colonoscopy suite. Additionally, cart (60) provides a mounting fixture for the present inventions effluent trap keeping it upright during the procedure. This maximizes its effectiveness by localizing any expelled liquid effluent/stool at the bottom of the trap away from the gas lumen. Also, the vertical height of the effluent reservoir is kept below the insufflator and exam table. Fixation of the effluent reservoir at a position lower than both the insufflator and individual facilitates the collection of effluent into the reservoir through gravity.

In one embodiment, insufflator (51) is an automatic insufflator unit. Automatic insufflator units suitable for use herein include, but are not limited to, any electronic device for displacing gas into the colon. In one embodiment, the unit is an electro-pneumatic carbon dioxide insufflator, such that the unit delivers $CO_2$ to the patient's colon for distention by specifying the following parameters at the control interface. When rectally inserting the enema tip of the disposable tube set in a patient, an appropriate distention pressure of $CO_2$ may include 0 to 25 mm Hg. Set flow rates of $CO_2$ may include about 1-20 L/mm, and set pressure from about 10 mm Hg to about 50 mm Hg, preferably about 3 to 6 L/mm, and 20-30 mm Hg, respectively.

In one embodiment, the insufflation system of the present invention is an E-Z-EM PROTOCO$_2$L™ ADMINISTRATION SET, or a similar system, used to displace and regulate $CO_2$ as a distention media to a patient's colon for purposes of CT colonography, or any other diagnostic procedure requiring colon distention. The PROTOCO$_2$L insufflator unit is based on currently marketed laparoscopic insufflator technology. This insufflator unit is a software controlled electromechanical system that precisely regulates pressure and meters flow of $CO_2$ from a supply cylinder to the patient. The PROTOCO$_2$L ADMINISTRATION SET comprising eight feet of vinyl tubing, two balloon inflators, plastic tubing clamp, Flexi-Tip with Flexi-Cuff silicone elastomer retention cuff; 0.1 micrometer hydrophobic filter, 100 mL effluent collection container, and connector to PROTOCO$_2$L Colon Insufflator. The system preferably provided in latex free form to prevent allergic reaction of the patient. Alternatively, the system described above may be used with any pneumatic manual insufflator, including the E-Z-EM hard bulb or E-Z-EM E-Z-Flat device, sold by E-Z-EM, Inc., Westbury, N.Y.

The present invention further relates to a method of collecting effluent discharged from the opening of an individual's body cavity administering a medium prior to or during a medical or diagnostic procedure. The method comprising one or more the following steps: (1) interfacing an effluent reservoir with an insertable member or other apparatus necessary to perform a medical or diagnostic procedure; (2) inserting the insertable member through the opening of an individual's body cavity; (3) performing a medical or diagnostic procedure while the insertable member is inserted in the individual's cavity, (4) collecting effluent passing through the opening of the individual's cavity into the effluent reservoir during or after the procedure; (5) manipulating the elevation of the effluent reservoir, if necessary, to facilitate passage of effluent into the effluent reservoir; (5) disconnecting the effluent reservoir from the insertable member or apparatus; and (6) engaging one or more clamps so as to prevent effluent from escaping the effluent reservoir during handling thereof.

Figure 15:
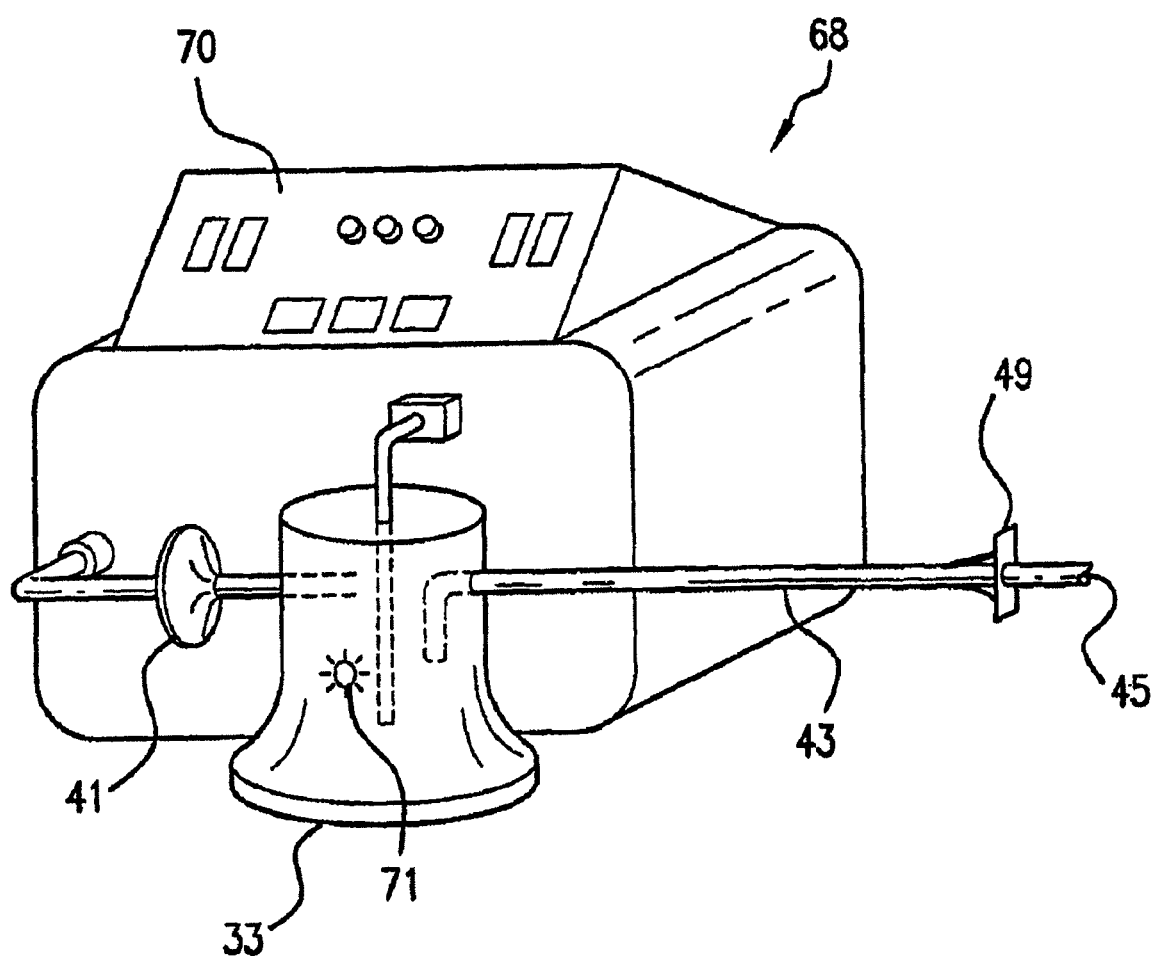
FIG. 15 shows an alternative embodiment of the present invention used in connection with an insufflator unit.
Figure 16:
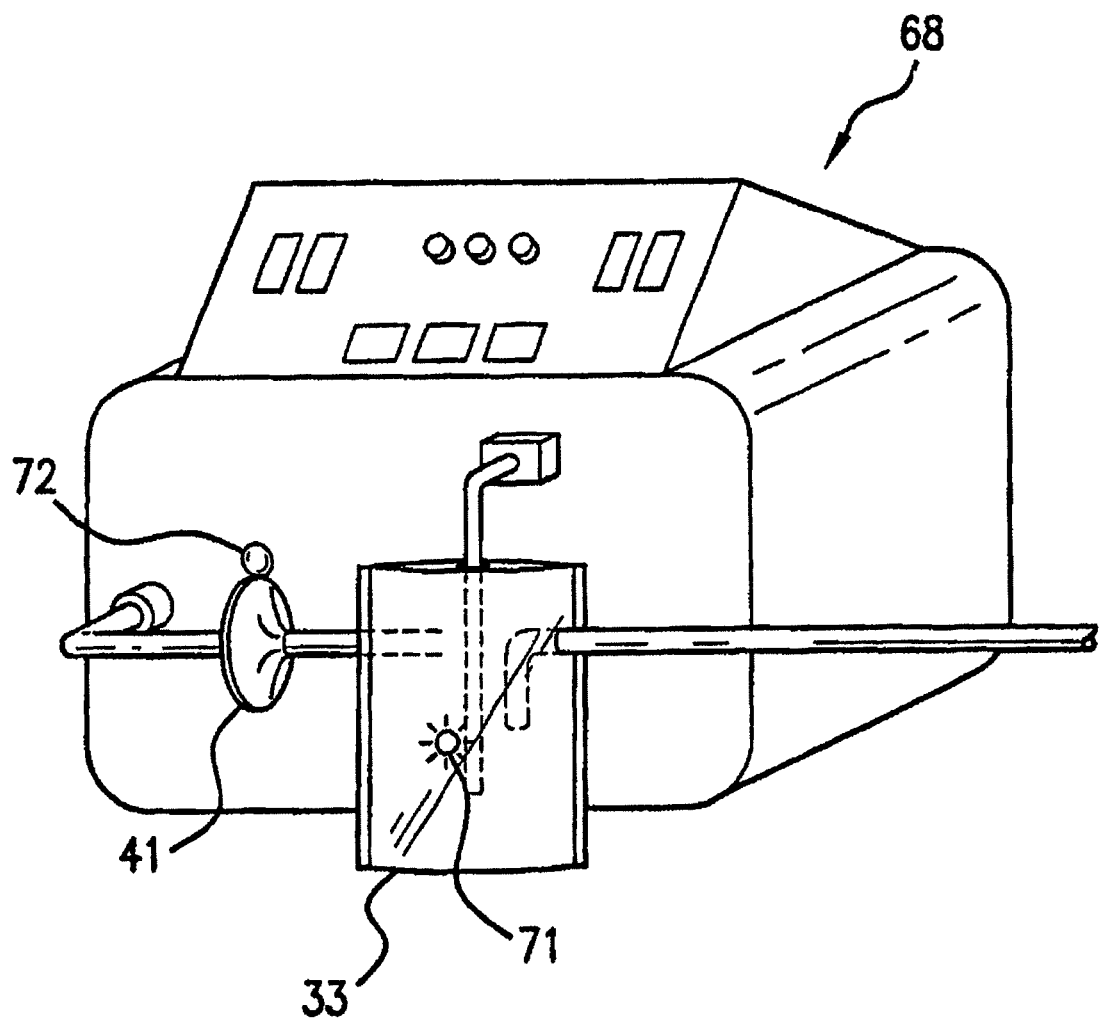
FIG. 16 shows an alternative embodiment of the present invention including sensors.

FIG. 15 illustrates an embodiment of the invention whereby the effluent trap is mounted to automatic insufflator (68) rather than an accessory cart. The figure illustrates a top mounted and tilted control panel (70) that will permit the operator to control it when it is positioned in a vertical position below the patient. The advantage of such an arrangement is the placement of a sensor (71), including but not limited electro-optical sensors adapted to detect the presence of an effluent prior to the administration of $CO_2$ to the patient. The purpose for such a sensor is two fold. First it prevents unintended operation of the device. Secondly, a sensing arrangement can be used to assure that an effluent reservoir is properly interfaced with the insufflator apparatus.

FIG. 16 again illustrates an embodiment of the invention whereby the effluent trap is mounted to automatic insufflator (68) rather than an accessory cart. In this figure, sensors (71) and (72) may comprise an electro-optical means. These sensors are used to detect the presence of the effluent trap and the hydrophobic filter, respectively. These sensors have the same purpose as that of the sensor used on the effluent trap shown in FIG. 15. Additionally, since medical hydrophobic filters are typically mounted in a rigid plastic housing, the front face of the insufflator that is now providing support for the effluent trap can now include geometric features to accept the geometry of the hydrophobic filter. This mounting arrangement for the filter, in conjunction with the sensor (electro-optical), can be designed to house filters having unique geometric attributes. Similarly, the placement of the filter electro-optic sensor (72) of FIG. 16 can be placed upstream/distal side of the membrane. With material properties of the administration set, the properties of the electro-optic sensor can be tuned such that the sensor can also detect a failure, namely breech of liquid across the filter membrane. An alternative sensing technology for serving this same purpose would be ultra-sonic.

Figure 17:
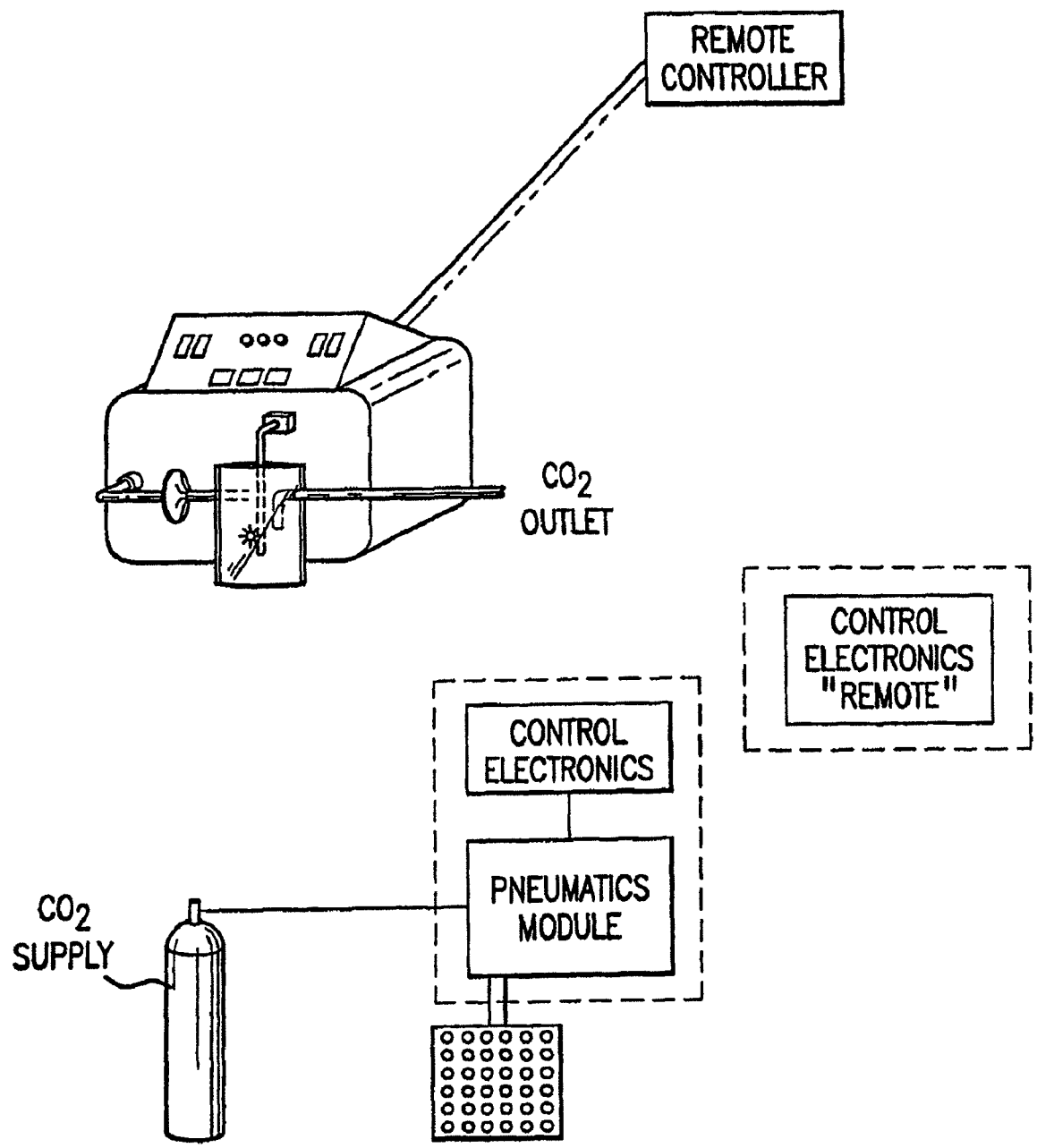
FIG. 17 shows an alternative embodiment of the present invention including a porous filter media.

FIG. 17 illustrates an embodiment of the invention whereby a porous filter media is attached to the venting port of an electro pneumatic insufflator. Such media may comprise activated charcoal or other scrubbing media that can be used to eliminate or minimize the escape of malodorous gas to the surrounding clinical atmosphere originating from the patient during the course of the procedure.

The figures and attachments herein are presented for illustrative purposes only. They are not intended to limit the scope of the invention. Further, it should be understood that various changes and modifications to the embodiment described herein will be apparent to those skilled in the art. Such changes and modifications can be made without departing from the spirit and scope of the present invention and without diminishing its attendant advantages. It is therefore intended that such changes and modifications be covered by the appended claims. Also, the invention may suitably comprise, consist of or consist essentially of the elements described herein. Further, the invention illustratively disclosed herein suitably may be practiced in the absence of any element which is or is not specifically disclosed herein.

The invention claimed is:

1. A device for collecting effluent from a gastrointestinal tract or abdominal cavity comprising:
   a member insertable into a gastrointestinal tract or abdominal cavity, and configured to allow fluid to flow into and out of the gastrointestinal tract or abdominal cavity;
   a reservoir configured to collect effluent from the gastrointestinal tract or abdominal cavity and disposed outside the gastrointestinal tract or abdominal cavity when the device is in use;
   a first conduit between the insertable member and the reservoir, wherein the insertable member, the first conduit, and the reservoir are positioned in succession;
   a second conduit having a first end attached to the reservoir and a second end provided with a connector that engages an insufflator apparatus, such that, in an operational state in which gas is emitted by the insufflator, the insufflator apparatus, the at least one connector, the second conduit, and the reservoir are positioned in succession;
   an effluent barrier positioned in cooperation with the second conduit to prevent effluent from contacting the insufflator, wherein, in the operational state, the gas flows from the insufflator to the second conduit, the reservoir, the first conduit, and the insertable member, and effluent drains from the gastrointestinal tract or abdominal cavity through the insertable member to the first conduit and into the reservoir.

2. The device of claim 1, wherein the reservoir comprises at least one connector means for interfacing the reservoir with the insertable member.

3. The device of claim 1, wherein the reservoir is a flexible, collapsible bag.

4. The device of claim 1, wherein the reservoir comprises a rigid container.

5. The device of claim 1, further comprising a sensor adapted to detect unintended operation of the device or improper connection of the reservoir to the insertable member.

6. The device of claim 1, further comprising a sensor adapted to detect a breach of fluid across one or more barriers.

7. The device of claim 1, wherein the insertable member defines an upper end and a lower end, wherein the upper end of the insertable member is rounded and is configured for insertion into the gastrointestinal tract or abdominal cavity and the lower end of the insertable member is configured to be secured to the reservoir so that, in the operational state, effluent passes through the insertable member and into the reservoir.

8. The device of claim 1, wherein the insertable member comprises a single lumen enema tip having a shaft, wherein said tip is insertable into the rectum of a patient.

9. A method for distending the colon of a patient in preparation for diagnostic imaging comprising insufflating the patient's colon with $CO_2$ using the device of claim 1 in conjunction with an automatic $CO_2$ insufflator apparatus.

10. A method for diagnostic imaging a region of interest internally of an individual comprising:
    (a) providing the device of claim 1;
    (b) inserting the insertable member into a gastrointestinal tract or abdominal cavity of the individual;
    (c) assuring that effluent and/or stool expelled from the individual is substantially drained and captured in the reservoir;
    (d) connecting the device to an automatic insufflation unit;
    (e) displacing air into the individual's gastrointestinal tract or abdominal cavity; and
    (f) scanning the region of interest with an imaging apparatus.

11. The method according to claim 10, wherein the region of interest is the colon.

12. The method according to claim 10, wherein the imaging apparatus comprises a CT imaging apparatus, MR imaging apparatus, or PET imaging apparatus.

13. The device according to claim 1 further comprising:
    an expandable member disposed on an exterior of the insertable member and configured to maintain the insertable member in a desired position within the gastrointestinal tract or abdominal cavity; and
    an inflation conduit in fluid communication with the expandable member, wherein the inflation conduit is configured to allow fluid to flow into and out of the expandable member for inflating and deflating, respectively, the expandable member,
    wherein, in an inflated configuration, the expandable member is configured to maintain the insertable member in the desired position within the gastrointestinal tract or abdominal cavity and wherein, in a deflated configuration, the expandable member is configured to allow the insertable member to pass into and out of the gastrointestinal tract or abdominal cavity.

14. The device of claim 13, wherein the inflation conduit is at least partially disposed along an interior of the insertable member.

15. The device of claim 13, wherein the inflation conduit is at least partially disposed along an exterior of the insertable member.

16. The device of claim 13, wherein the insertable member comprises a main lumen, wherein the inflation conduit branches into and extends within the main lumen.

17. The device of claim 13, wherein the expandable member is an annular expandable member fixed to and encircling the insertable member and is configured to be expanded outwardly to circumferentially surround the insertable member.

18. The device of claim 1, wherein the reservoir comprises a rigid container or jar.

19. A device for collecting effluent from a gastrointestinal tract or abdominal cavity comprising:
    an insertable member configured to be inserted into a gastrointestinal tract or abdominal cavity, and further configured to allow fluid to flow into and out of the gastrointestinal tract or abdominal cavity;
    an expandable member disposed on an exterior of the insertable member and configured to maintain the insertable member in a desired position within the gastrointestinal tract or abdominal cavity;
    an inflation conduit in fluid communication with the expandable member, wherein the inflation conduit is configured to allow fluid to flow into and out of the expandable member for inflating and deflating, respectively, the expandable member;
    a reservoir configured to collect effluent from the gastrointestinal tract or abdominal cavity;
    a first conduit longitudinally positioned between and in fluid communication with the insertable member and the reservoir such that the insertable member, the first conduit, and the reservoir are positioned in succession; and
    a second conduit attached at one end to the reservoir and having at least one connector configured to connect to an insufflator apparatus, such that, in an operational state in which gas is emitted by the insufflator, the insufflator apparatus, the at least one connector, the second conduit, and the reservoir are positioned in succession;
    wherein, in the operational state, the gas flows from the insufflator to the reservoir, the first conduit, and the insertable member into the gastrointestinal tract or abdominal cavity, and wherein the effluent drains from the gastrointestinal tract or abdominal cavity through the insertable member to the first conduit and into the reservoir, and
    wherein, in an inflated configuration, the expandable member is configured to maintain the insertable member in the desired position within the gastrointestinal tract or abdominal cavity and wherein, in a deflated configuration, the expandable member is configured to allow the insertable member to pass into and out of the gastrointestinal tract or abdominal cavity.

20. The device of claim 19, wherein the expandable member is an annular expandable member fixed to and encircling the insertable member and is configured to be expanded outwardly to circumferentially surround the insertable member.

* * * * *